United States Patent [19]
Gentile et al.

[11] Patent Number: 6,030,985
[45] Date of Patent: *Feb. 29, 2000

[54] AMIDINE DERIVATIVES WITH NITRIC OXIDE SYNTHETASE ACTIVITIES

[75] Inventors: Robert James Gentile, Scotsville; Robert John Murray, Brighton; James Edwin MacDonald, Pittsford; William Calvin Shakespeare, Rochester, all of N.Y.

[73] Assignee: Astra Aktiebolag, Sodertalje, Sweden

[*] Notice: This patent is subject to a terminal disclaimer.

[21] Appl. No.: 09/111,926

[22] Filed: Jul. 8, 1998

Related U.S. Application Data

[62] Division of application No. 08/586,761, filed as application No. PCT/GB94/01767, Aug. 12, 1996, Pat. No. 5,807,885.

[30] Foreign Application Priority Data

| Aug. 12, 1993 | [GB] | United Kingdom | 9316806 |
| Sep. 25, 1993 | [GB] | United Kingdom | 9319835 |
| Dec. 11, 1993 | [GB] | United Kingdom | 9325410 |
| Jan. 27, 1994 | [GB] | United Kingdom | 9401580 |
| Jun. 10, 1994 | [GB] | United Kingdom | 9411700 |

[51] Int. Cl.$^7$ .............. A61K 31/47; A61K 31/445; A61K 31/40; A61K 31/38; A61K 31/155

[52] U.S. Cl. .............. 514/307; 514/326; 514/427; 514/438; 514/637

[58] Field of Search .............. 514/307, 326, 514/427, 438, 637

[56] References Cited

U.S. PATENT DOCUMENTS

| 3,299,081 | 1/1967 | Sletzinger et al. . | |
| 3,669,974 | 6/1972 | Elpern et al. . | |
| 5,266,594 | 11/1993 | Dawson et al. | 514/560 |

FOREIGN PATENT DOCUMENTS

| 0 446 699 | 2/1991 | European Pat. Off. . |
| 0 547 558 | 12/1992 | European Pat. Off. . |
| 2 321 330 | 4/1973 | Germany . |
| 5 857 357 | 9/1981 | Japan . |
| 2 229 147 | 3/1989 | Japan . |
| 1 088 095 | 10/1964 | United Kingdom . |
| 1 180 629 | 7/1968 | United Kingdom . |
| 2 226 562 | 12/1989 | United Kingdom . |
| 9 104 024 | 9/1989 | WIPO . |
| 9 204 054 | 8/1990 | WIPO . |
| 9 216 666 | 3/1991 | WIPO . |
| 9 412 797 | 3/1991 | WIPO . |
| 9 324 126 | 5/1992 | WIPO . |
| 9 313 055 | 12/1992 | WIPO . |
| 9 412 163 | 11/1993 | WIPO . |
| 9 412 165 | 11/1993 | WIPO . |
| 9 421 621 | 3/1994 | WIPO . |

OTHER PUBLICATIONS

Moncada et al, "Nitric oxide; Physiology, . . . " Pharmacological Reviews, vol. 43, pp. 109–142 (1991).

Nissan Chem. Ind. KK (1989) "Fluorine–contg cpds." (0–38310/42).

Forstermann et al, "Induced RAW 264.7 macrophages express," European J. of Pharmacology–Molec. Pharmac. Sect. vol. 225, pp. 161–165 (1992).

Bredt et al, "Isolation of nitric oxide synthetase . . . ," Proc. Natl. Acad. Sci. (USA), vol. 87, pp. 682–685 (1990).

Pollock et al, "Purification and characterization of . . . ," Proc. Natl. Acad. Sci. (USA), vol. 88, pp. 10480–10484 (1991).

Primary Examiner—William R. A. Jarvis
Attorney, Agent, or Firm—Nixon & Vanderhye

[57] ABSTRACT

The present invention relates to methods and compositions useful for treating and preventing conditions in which inhibition of nitric oxide synthetase is beneficial. These conditions include stroke, schizophrenia, anxiety, and pain.

18 Claims, No Drawings

AMIDINE DERIVATIVES WITH NITRIC OXIDE SYNTHETASE ACTIVITIES

This application is a divisional of application Ser. No. 08/586,761, filed Jan. 30, 1996, now U.S. Pat. No. 5,807,885, which is a 371 of PCT/GB94/01767, filed Aug. 12, 1994.

This invention relates to amidine derivatives, processes for their preparation, compositions containing them and their use in therapy.

Certain nitrogen containing compounds have been described as neuroprotective agents. International Patent Application WO 91/12797 (State of Oregon) teaches tri- and tetrasubstituted guanidines as neuroprotective agents. U.S. Pat. No. 5,266,694 (Dawson et al) (published after the earliest priority date of this application) describes the use of arginine derivatives in the treatment of stroke and other neurodegenerative diseases. Also European Patent Application 547558 (Washington University) describes the use of aminoguanidine in the treatment of immunological and other disorders.

The use of inhibitors of nitric oxide synthetase in the treatment of disease has also been described, for example, in International Patent Applications WO 94/12163 (Abbott) and WO 94/12165 (Wellcome) (both published after the earliest priority date of this application) and European Patent Application 446699 (Merrell Dow).

Amidine derivatives have been described for use as herbicides in German Patent Application DE-OS-2321330 (Bayer). N-phenyl amidine derivatives have also been described for use in the treatment of diabetes in U.S. Pat. No. 3,669,974 (USV Pharmaceutical Corp.) and UK Patent Application 2226562 (Boots). N'N"-disubstituted amidines are described for us in the treatment of hypertension, depression and halliconogenic states in International Patent Application WO 92/04054 (University of Oregon). The use of certain symmetric bisamidines as analgesics, in the treatment of inflammation and in the treatment of hypertension is described in UK Patent No. 1180629 (Delalande).

A number of patent documents describe processes for the preparation of amidines or describe the use of amidines as intermediates without disclosing any pharmaceutical use of these compounds. Simple amidine derivatives are described in UK Patent No. 1088095 (Merck) as intermediates in the preparation of useful benzimidazole derivatives. Processes for preparation of other simple N-aryl and N-heteroaryl amidines are described in U.S. Pat. No. 3,299,081 (Merck) and flourine containing amidine derivatives are described as chemical intermediates in Japanese Patent Application No. 2229147 (Nissan) and in Japanese Patent Application No. 58057357 (Daikin).

We have now found a new group of amidine derivatives that possess useful pharmaceutical activity.

According to a first aspect of the invention, we provide a compound of formula I

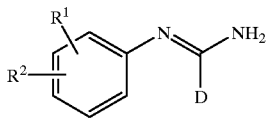

wherein D represents phenyl, pyridinyl or a 5 membered heterocyclic aromatic ring containing 1 to 4 heteroatoms selected from O, S and N, which three groups are optionally substituted by one or more groups selected from alkyl C1 to 6, alkoxy C1 to 6, halogen and perfluoroalkyl C1 to 6; or perfluoroalkyl C1 to 6; $R^1$ represents hydrogen, alkyl C1 to 6 or halogen; $R^2$ represents —X(CH$_2$)$_n$ZCONR$^3$R$^4$, —X(CH$_2$)$_n$NHCO(CH$_2$)$_n$NR$^3$R$^4$, —X(CH$_2$)$_p$NR$^3$R$^4$, —X(CH$_2$)$_s$NHCOR$^5$ or —((CH$_2$)$_q$NHC(NR)R$^6$; $R^3$ and $R^4$ independently represent hydrogen, alkyl C1 to 6, —(CH$_2$)$_r$A, —(CH$_2$)$_m$OA or —CH(CH$_3$)(CH$_2$)$_r$A; or —NR$^3$R$^4$ together represent 1-indanyl, piperonylamino-, piperidinyl, morpholinyl, pyrrolidinyl, 1,2,3,4-tetrahydroisoquinolinyl; or piperazinyl optionally 4-substituted by alkyl C1 to 6; $R^5$ represents alkyl C1to 6, perfluoroalkyl C1 to 6, —(CH$_2$)$_r$A or —O(CH$_2$)$_w$A; A represents phenyl, pyridinyl, pyrimidinyl, or a 5 membered heterocyclic aromatic ring containing 1 to 4 heteroatoms selected from O, S and N, which four groups are optionally substituted by one or more groups selected from alkyl C1 to 6, halogen nitro, cyano and trifluoromethyl; $R^6$ represents phenyl, pyridinyl or a 5 membered heterocyclic aromatic ring containing 1 to 4 heteroatoms selected from O, S and N, which three groups are optionally substituted by one or more groups selected from alkyl C1 to 6, alkoxy C1 to 6, halogen and perfluoroalkyl C1 to 6; or perfluoroalkyl C1 to 6; n and r independently represent an integer in the range 1 to 6 inclusive; p and w independently represent an integer in the range 1 to 5 inclusive; m represents an integer in the range 2 to 5 inclusive; q and t independently represent an integer in the range 0 to 5 inclusive; s represents an integer in the range 1 to 3 inclusive; X represents O or a bond; Z represents O, NR$^7$ or a bond; $R^7$ represents hydrogen or alkyl C1 to 6; provided that:

(a) when D contains a heteroatom, it is not connected to the remainder of the compound of formula I through the heteroatom;

(b) when $R^2$ represents —X(CH$_2$)$_n$ZCONR$^3$R$^4$ and neither X nor Z represent a bond, then n represents an integer in the range 2 to 6 inclusive;

(c) when $R^2$ represents —X(CH$_2$)$_s$NHCO(CH$_2$)$_s$NR$^3$R$^4$ or —X(CH$_2$)$_s$NHCOR$^5$, and X represents O then n represents an integer in the range 2 to 6 inclusive;

(d) when $R^2$ represents —X(CH$_2$)$_p$NR$^3$R$^4$ X represents O, then p represents an integer in the range of 2 to 5 inclusive;

(e) when $R^2$ represents —(CH$_2$)$_q$NHC(NH)R$^6$, $R^1$ represents hydrogen, D represents phenyl and $R^6$ represents phenyl, then q does not represent 0;

(f) when $R^2$ represents —(CH$_2$)$_q$NHC(NH)R$^6$, $R^1$ represents hydrogen, D and $R^6$ represent 2-chlorophenyl, then q does not represent 0;

(g) when $R^2$ represents —(CH$_2$)$_q$NHC(NH)R$^6$, $R^1$ represents hydrogen, D and $R^6$ represent 3-pyridinyl, then q does not represent 0; and (h) when $R^2$ represents —(CH$_2$)$_q$NHC(NH)R$^6$, $R^1$ represents hydrogen, D and $R^6$ represent 4-pyridinyl, then q does not represent 0; or a pharmaceutically acceptable salt thereof.

We prefer that D represents phenyl, pyridinyl or a 5 membered heterocyclic aromatic ring containing 1 to 4 heteroatoms selected from O, S and N, which three groups are optionally substituted by one or more groups selected from alkyl C1 to 6, alkoxy C1 to 6, halogen or perfluoroalkyl C1 to 6.

We particularly prefer that D represents phenyl, thiophene, furan, pyrrole or thiazole, which five groups are optionally substituted by one or more groups selected from alkyl C1 to 6, alkoxy C1 to 6, halogen or perfluoroalkyl C1 to 6.

We more particularly prefer that D represents thiophene, pyrrole, furan or thiazole which four groups are optionally substituted by alkyl C1 to 6 or halogen.

We especially prefer than D represents thiophene, furan or pyrrole, most especially thiophene.

We prefer most of all that D represents 2-thiophene.

We prefer that $R^1$ represents hydrogen.

When $R^2$ represents $-X(CH_2)_sZCONR^3R^4$, $-X(CH_2)_sNHCO(CH_2)_sNR^3R^4$ or $-X(CH_2)_pNR^3R^4$, we prefer that $-NR^3R^4$ represents piperidinyl, morpholinyl, pyrrolidinyl, 1,2,3,4-tetrahydroisoquinolinyl or 1-indanyl, or that at least one of $R^3$ and $R^4$ represents $-(CH_2)_rA$ or $-(CH_2)_mOA$. We particularly prefer that $-NR^3R^4$ represents 1,2,3,4-tetrahydroisoquinolinyl or 1-indanyl or that one of $R^3$ and $R^4$ represents $-(CH_2)_rA$ and the other represents hydrogen or methyl. We especially prefer that one of $R^3$ and $R^4$ represents $-(CH_2)_rA$ and the other represents hydrogen or methyl.

When $R^2$ represents $-X(CH_2)_sNHCOR^5$, we prefer that $R^5$ represents $-(CH_2)_rA$.

When $R^2$ represents $-X(CH_2)_sZCONR^3R^4$, $-X(CH_2)_sNHCO(CH_2)_sNR^3R^4$, $-X(CH_2)_pNR^3R^4$ or $-X(CH_2)_sNHCOR^5$, we prefer X to represent a bond.

When $R^2$ represents $-X(CH_2)_nZCONR^3R^4$ and Z represents $NR^7$, we prefer $R^7$ to represent hydrogen.

When $R^2$ represents $-X(CH_2)_nZCONR^3R^4$ we prefer Z to represent a bond.

When $R^2$ represents $-(CH_2)_qNHC(NH)R^6$, we prefer that $R^6$ represents phenyl or a 5-membered heterocyclic aromatic ring containing 1 to 4 heteroatoms selected from O, S and N, which two groups are optionally substituted by one or more groups selected from alkyl C1 to 6, alkoxy C1 to 6 and halogen.

When $R^2$ represents $-(CH_2)_qNHC(NH)R^6$, we particularly prefer that $R^6$ represents phenyl or thiophene, which two groups are optionally substituted by one or more groups selected from alkyl C1 to 6 and halogen.

When $R^2$ represents $-(CH_2)_qNHC(NH)R^6$, we prefer that q represents n 0, 1 or 2. We particularly prefer that q represents 0 or 2, especially 0.

When $R^2$ represents $-(CH_2)_qNHC(NH)R^6$, q represents 0 and $R^6$ represents phenyl optionally substituted by halogen, alkyl C1 to 6, or alkoxy C1 to 6 or $R^6$ represents pyridinyl, then we prefer that D does not have the same definition as $R^6$.

When $R^2$ represents $-(CH_2)_qNHC(NH)R^6$ and q represents 0, then we generally prefer that $R^6$ does not have the same definition as D.

When $R^2$ represents $-X(CH_2)_pNR^3R^4$ we prefer that p represents an integer in the range 1 to 4 inclusive, particularly 1, 2 or 3, especially 1 or 2.

When $R^2$ represents $-X(CH_2)_sZCONR^3R^4$, $-X(CH_2)_sNHCO(CH_2)_sNR^3R^4$ or $-X(CH_2)_sNHCOR^5$, we prefer n to represent 1, 2 or 3, especially 2 or 3.

When $R^3$, $R^4$ or $R^5$ represent $-(CH_2)_rA$, we prefer r to represent an integer in the range 0 to 4 inclusive, particularly 0, 1 or 2, more particularly 1 or 2, especially 1.

When $R^3$ or $r^4$ represent $-(CH_2)_mOA$, we prefer m to represent 2, 3 or 4.

When $R^5$ represents $-O(CH_2)_wA$, we prefer w to represent 2, 3 or 4.

When $R^3$ or $R^4$ represent $-CHMe(CH_2)_tA$, we prefer t to represent 0, 1 or 2, especially 0 or 1.

We prefer that A represents phenyl, pyridinyl, pyrimidinyl, thiophenyl or furanyl, which five groups are optionally substituted by one or more groups selected from alkyl C1 to 6 and halogen. We particularly prefer that A represents phenyl optionally substituted one or more groups selected from alkyl C1 to 6 and halogen.

When D or $R^5$ represent perfluoroalkyl C1 to 6 we prefer that they represent pentafluoroethyl or trifluoromethyl, especially trifluoromethyl.

We prefer that $R^2$ represents $-X(CH_2)_pNR^3R^4$ or $-(CH_2)_qNHC(NH)R^6$.

We prefer that the orientation of $R^2$ is meta or para to the nitrogen atom of the amidine moiety.

According to the invention, we further provide a process for the preparation of compounds of formula I, and pharmaceutically acceptable salts thereof, which comprises:

(a) preparing a compound of formula I, by reacting a corresponding compound of formula II

II wherein D is as defined above and L is a leaving group, with a compound of formula III

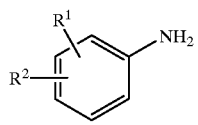

III wherein $R^1$ and $R^2$ are as defined above, (b) preparing a compound of formula I, by reacting a corresponding compound of formula IV

IV wherein D is as defined above, with a compound of formula V

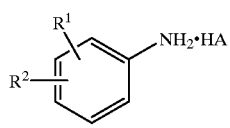

V wherein $R^1$ and $R^2$ are as defined above and HA is an acid, (c) preparing a compound of formula I in which $R^2$ represents $-X(CH_2)_nZCONR^3R^4$, $-X(CH_2)_pNR^3R^4$ and at least one of $R^3$ and $R^4$ represents alkyl C1 to 6, $-(CH_2)_mOA$ or $-CH(CH_3)(CH_2)_t$ by reacting a corresponding compound of formula I in which one or both of $R^3$ and $R^4$ represents hydrogen with a compound of formula VI,

VI wherein $R^4$ represents alkyl C1 to 6, $-(CH_2)_rA$, $-(CH_2)_mOA$ or $-CH(CH_3)(CH_2)_rA$ and L is a leaving group, (d) preparing a compound of formula I in which $R^2$ represents $-(CH_2)_qNHC(NH)R^4$ by reacting a corresponding compound of formula VII

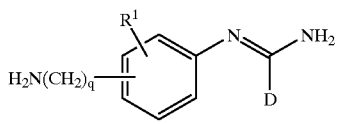
VII wherein D, R¹ and q are as defined above, with a compound of formula VIII

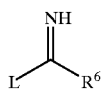
VIII wherein R⁶ is a defined above and L is a leaving group, (e) preparing a compound of formula I in which R² represents —(CH$_2$)$_q$NHC(NH)R⁶ by reacting a corresponding compound of formula IX

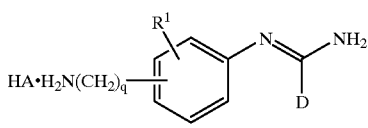
IX wherein D, R¹, q and HA are as defined above, with a compound of formula X

X wherein R⁶ is as defined above, (f) preparing a compound of formula I in which R² represents —X(CH$_2$)$_n$ZCONR³R⁴ by reacting a corresponding compound of formula XI,

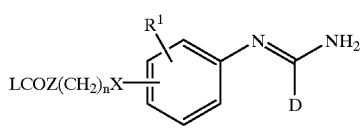
XI wherein D, R¹, X, n, Z and L are as defined above, with a compound of formula XII,

XII wherein R³ R⁴ are as defined above, (g) preparing a compound of formula I in which R² represents —X(CH$_2$)$_n$NHCO(CH$_2$)$_s$NR³R⁴, by reacting a compound of formula XIII

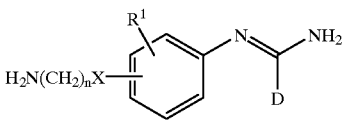
XIII wherein D, R¹, X and n are as defined above, with a compound of formula XIV

XIV wherein R³, R⁴ and s are as defined above and L is a leaving group, (h) preparing a compound of formula I in which R² represents —X(CH$_2$)$_n$NHCOR⁵, by reacting a compound of formula XIII with a compound of formula XV

R⁵COL      XV wherein R⁵ is as defined above and L is a leaving group, (i) preparing a compound of formula I in which R² represents —X(CH$_2$)$_s$ZCONR³R⁴ and Z represents NR⁷ by reacting a corresponding compound of formula I in which R² represents —X(CH$_2$)$_n$ZCONR³R⁴ represents —NH with a compound of formula XVI

XVI wherein R⁷ is as defined above and L is a leaving group, (j) preparing a compound of formula I in which R² represents —X(CH$_2$)$_p$NR³R⁴, and p is not less than 2, by reduction of a compound of formula XVII

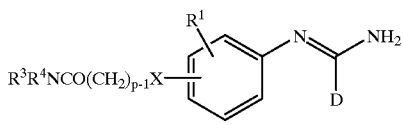
XVII wherein D, X, R¹, R³, R⁴ and p are as defined above, (k) preparation of a compound of formula I wherein R² represents —X(CH$_2$)$_p$NR³R⁴ and both R³ and R⁴ represent hydrogen, by reduction of a corresponding compound of formula XVIII

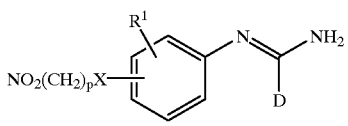
XVIII wherein R¹, D, p and X are as defined above, (l) preparing a compound of formula I wherein R² represents —X(CH$_2$)$_n$ZCONR³R⁴, Z represents O or NR⁷ and R³ represents hydrogen by reacting a compound of formula XIX

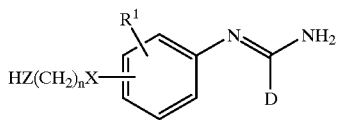

XIX wherein $R^1$, D, X and n are as defined above and Z represents O or $NR^7$, with a compound of formula XX $$R^4\text{—}N\text{=}C\text{=}O) \qquad \qquad XX$$

wherein $R^4$ is as defined above, (m) preparing a compound of formula I wherein $R^2$ represents —$X(CH_2)_n NHCOR^5$ and $R^5$ represents —$O(CH_2)_w A$ by reacting a compound of formula XXI

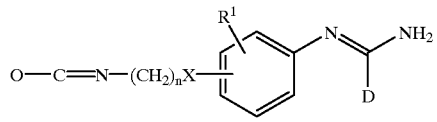

XXI wherein $R^1$, D, X and n are as defined above, with a compound of formula XXII $$A(CH_2)_w OH \qquad \qquad XXII$$

wherein A and w are as defined above, (n) preparing a compound of formula I wherein $R^2$ represents —$X(CH_2)_n ZCONR^3 R^4$ and Z represents O or $NR^7$ by reacting a compound of formula XIX with a compound of formula XXIII

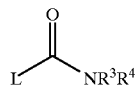

XXIII wherein $R^3$ and $R^4$ are as defined above, (o) preparing a compound of formula I wherein $R^2$ represents —$X(CH_2)_p NR^3 R^4$, $R^3$ represents hydrogen and p represents an integer 2 to 5, by reduction of a compound of formula XXIV

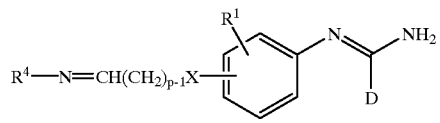

XXIV wherein $R^1$, $R^4$, D, X and p are as defined above, (p) preparing a compound of formula I wherein $R^2$ represents —$X(CH_2)_p NR^3 R^4$, one of $R^3$ and $R^4$ represents hydrogen, and the other represents —$(CH_2)_r A$ in which r represents an integer 2 to 6, by reduction of a compound of formula XXV

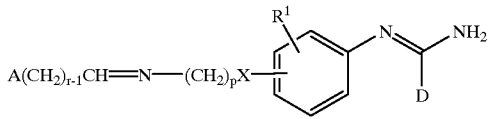

XXV wherein $R^1$, A, D, r and p are as defined above, (q) preparing a compound of formula I wherein $R^2$ represents —$X(CH_2)_p NR^3 R^4$, one of $R^3$ and $R^4$ represents hydrogen, and the other represents —$(CH_2)_m OA$, by reduction of a compound of formula XXVI

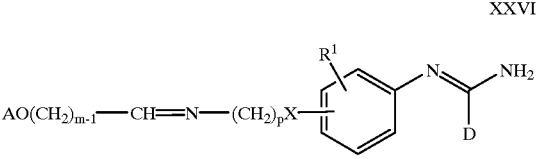

XXVI wherein $R^1$, A, D, p and m are as defined above, (r) preparing a compound of formula I wherein $R^2$ represents —$X(CH_2)_p NR^3 R^4$, one of $R^3$ and $R^4$ represents hydrogen, and the other represents —$(CH_2)_r A$ in which r represents an integer 2 to 6, by reduction of a compound of formula XXVII

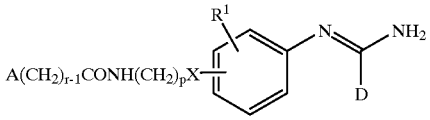

XXVII wherein $R^1$, A, D, p and r are as defined above, or (s) preparing a compound of formula I wherein $R^2$ represents —$X(CH_2)_p NR^3 R^4$, one of $R^3$ and $R^4$ represents hydrogen, and the other represents —$(CH_2)_m OA$, by reduction of a compound of formula XXVIII

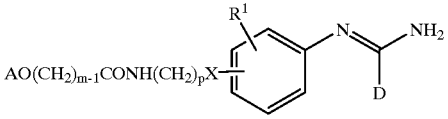

XXVIII wherein $R^1$, A, D, p and m are as defined above, and where desired or necessary converting the resultant compound of formula I, or another salt thereof, to a pharmaceutically acceptable salt thereof, or vice versa.

In process (a), the reaction will take place on stirring a mixture of the reactants in a suitable solvent for example a lower alkanol e.g. ethanol, isopropanol or tertiary butanol, at a temperature between room temperature and the reflux temperature of the solvent. The reaction time will depend inter alia on the solvent and the nature of the leaving group, and may be up to 48 hours, however it will typically be from 1 to 5 hours. Suitable leaving groups that L may represent include thioalkyl, sulphonic acid, trifluorocarbon sulphonic acid, halide, alkyl and aryl alcohols and tosyl groups; others are recited in 'Advanced Organic Chemistry', J. March (1985) 3rd Edition, McGraw-Hill on page 315 and are well known in the art.

In process (b), the reaction is preferably performed by refluxing a mixture of the two compounds for several hours in the presence of a suitable solvent whereby the reaction temperature is high enough so that condensation takes place readily, but not sufficiently high to decompose the amidine formed. The reaction temperature can vary from room temperature to about 250° C., although it is preferable to perform the reaction at temperatures from about 100° C. to 200° C. We find that o-dichlorobenzene is a particularly suitable solvent and it is useful to add 4-dimethylaminopyridine as a catalyst. On cooling, two layers form, the solvent may be decanted, and the reaction worked up by addition of aqueous base. Alternatively, where the reactants are soluble in the solvent, the solvent may be evaporated off under vacuum and the reaction mixture worked up by addition of water. The acid HA may be an organic or inorganic acid, for instance, hydrochloric, hydrobromic, hydroiodic, sulphuric, nitric, phosphoric, acetic, lactic, succinic, fumaric, malic, maleic, tartaric, citric, benzoic or methanesulphonic acid.

In process (c), the reaction will take place under standard conditions, for example by reacting the two materials in an inert solvent under basic conditions at room temperature for a period of up to 12 hours. We have frequently found it desirable to treat the amine with NaH before reacting with the compound of formula II. We prefer that L represents halide, particularly bromide.

Process (d) may be performed under conditions analogous to those described above for process (a).

Process (e) may be performed under conditions analogous to those described above for process (b).

Processes (f), (g) and (h) may be performed under the standard conditions well known in the art for condensation of an amine and a carboxylic acid or an activated carboxylic acid to form an amide. For example, reaction of compounds to form the amide may be achieved on stirring the reactants for 12–24 hours at a temperature between 0° C. and 25° C. in water or a mixture of water and a less polar solvent, for example dioxan, tetrahydrofuran or ethanol. We prefer to perform the reaction under basic conditions, e.g. in the presence of aqueous sodium carbonate or sodium bicarbonate.

Process (i) may be performed under standard conditions analogous to those given above for process (c).

In process (j), the reduction may be performed by treatment with diborane in an inert solvent e.g. THF. Alternative although less preferred reagents which may be suitable include lithium aluminium hydride and reagents for catalytic hydrogenation e.g. $H_2$ on Pd/C. Further details of the reaction conditions for use of these reactions may be obtained by reference to J. March "Advanced Organic Chemistry" on page 1099, including the references cited therein.

In process (k), the reduction reaction may be performed under a number of conditions, for example those described in J. March "Advanced Organic Chemistry" on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure for 3–6 hours in the presence of a palladium and carbon catalyst.

In process (l) and (m), the reaction may be performed by stirring the reactants in the presence of an inert solvent at a temperature between room temperature and the reflux temperature of the solvent for up to 24 hours.

Process (n) may be performed under conditions analogous to those described above for processes (f), (g) and (h).

In processes (o), (p) and (q), the reduction may be performed by treating the compound with sodium borohydride under standard conditions.

In processes (r) and (s), the reaction may be performed under conditions analogous to those described above for process (j).

Salts of compounds of formula I may be formed by reacting the free acid, base or a salt, enantiomer, tautomer or protected derivative thereof, with one or more equivalents of the appropriate base or acid. The reaction may be carried out in a solvent or medium in which the salt is insoluble or in a solvent in which the salt is soluble, eg water, dioxan, ethanol, tetrahydrofuran or diethyl ether, or a mixture of solvents, which may be removed in vacuo or by freeze drying. The reaction may be a metathetical process or it may be carried out on an ion exchange resin.

It will be apparent to a person skilled in the art that it may be desirable to protect a hydroxy, amine or other reactive group using a protecting group as described in the standard text "Processing groups in Organic Synthesis", 2nd Edition (1991) by Greene and Wuts. Amine-protecting groups which may be mentioned include alkyloxycarbonyl C2 to 7, eg t-butyloxycarbonyl, phenylalkyloxycarbonyl C8 to 13, eg benzyloxycarbonyl or preferably trifluoroacetate. Deprotection will normally take place on treatment with aqueous base.

Compounds of formula II are either known or may be prepared by known methods. For example, compounds of formula II in which L represents thioalkyl may be prepared by treatment of the corresponding thiamide of formula XXIX

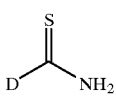

XXIX wherein D is as defined above, with an alkyliodide.

The compounds of formula III may be prepared by reduction of a corresponding compound of formula XXX

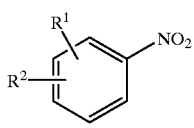

XXX wherein $R^1$ and $R^2$ are as defined above.

The reduction reaction may be performed under analogous conditions to those described above for process (k).

Certain compounds of formula XXX are either known or may be prepared by conventional methods known per se. Other compounds of formula XXX may be prepared from known compounds with simpler side-chains by following analogous processes to those described above for processes (c) to (s).

Compounds of formula V may be prepared by analogous processes to those described for the preparation of compounds of formula III. Compounds of formula V may be converted to corresponding compounds of formula III by treatment with a base. Compounds of formula III may be converted to corresponding compounds of formula V by treatment with a protic acid HA, for example one of those listed above.

Compounds of formula VII, IX, XI, XIII, XVII, XVIII, XIX, XXI, XXIV, XXV, XXVI, XXVII and XXVIII may be prepared by analogous processes to those described for the preparation of compounds of formula I.

Compounds of formula VIII are either known or may be prepared by an analogous process to that described above for preparation of compounds of formula II.

Compounds of formula IV, VI, X, XII, XVI, XX, XXII, XXIII and XXIX are either known or may be prepared by conventional methods known per se.

Compounds of formula XIV and XV are either known or may readily be prepared from the corresponding carboxylic acid which is either known or may be prepared by conventional methods known per se.

Where necessary, hydroxy, amine or other reactive groups in intermediate compounds may be protected using a protecting group as described in the standard text "Protecting groups in Organic Synthesis", 2nd Edition (1991) by Greene and Wuts.

The compounds of the invention and intermediates may be isolated from their reaction mixtures by standard techniques.

The term "alkyl C1 to 6" includes straight chain, branched, saturated, unsaturated, aliphatic and cyclic alkyl groups containing 1 to 6 carbon atoms.

The compounds of formula I may exist in tautomeric, enantiomeric or diasteriomeric forms, all of which are included within the scope of the invention. The various optical isomers may be isolated by separation of a racemic mixture of the compounds using conventional techniques, e.g. fractional crystallisation, or HPLC. Alternatively the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

The compounds of general formula I posses useful pharmacological activity in animals. In particular, they posses useful nitric oxide synthetase inhibiting activity, and are expected to be useful in the treatment or prophylaxis of human diseases or conditions in which the synthesis or oversynthesis of nitric oxide forms a contributory part; for example, hypoxia, e.g. in cases of cardiac arrest and stroke, neurodegenerative disorders including nerve degeneration and/or nerve necrosis in disorders such as hypoxia, hypoglycemia, epilepsy, and in external wounds (such as spinal cord and head injury), hyperbaric oxygen convulsions and toxicity, dementia e.g. pre-senile dementia, Alzheimer's disease and AIDS-related dementia, Sydenham'chorea, Parkinson's disease, Huntington's disease, Amyotrophic Lateral Sclerosis, Korsakoff's disease, imbecility relating to a cerebral vessel disorder, sleeping disorders, schizophrenia, depression, seasonal affective disorder, jet-lag, depression or other symptons associated with Premenstrual Syndrome (PMS), anxiety and septic shock. Compounds of formula I may also be expected to show activity in the prevention and reversal of tolerance to opiates and diazepines, treatment of drug addiction, relief of pain and treatment of migraine and other vascular headaches. The compounds of the present invention may also show useful immunosuppressive activity, be useful in the treatment or prophylaxis of inflammation, in the treatment of of gastrointestinal motility disorders, and in the induction of labour.

Compounds of formula I are expected to be particularly useful in the treatment of neurodegenerative disorders or of migraine or for the prevention and reversal of tolerance to opiates and diazepines of for the treatment of drug addiction and especially in the treatment of neurodegenerative disorders.

Thus according to a further aspect of the invention we provide a compound of formula I, or a pharmaceutically acceptable salt thereof, for use as a pharmaceutical.

According to another feature of the invention we provide the use of a compound of formula I, without provisos (e) to (h), or a pharmaceutically acceptable salt thereof, in the manufacture of a medicament for the treatment of the aforementioned diseases or conditions.

For the above mentioned therapeutic indications, the dosage administered will, of course, vary with the compound employed, the mode of administration and the treatment desired. However, in general, satisfactory results are obtained when the compounds are administered to a human at a daily dosage of between 1 mg and 2000 mg (measured as the solid form) per day.

The compounds of formula I, and pharmaceutically acceptable salts thereof, may be used on their own, or in the form of appropriate medicinal preparations for enteral or parenteral administration.

According to the invention, there is provided a pharmaceutical formulation including preferably less than 80% and more preferably less than 50% of a compound of formula I, or a pharmaceutically acceptable salt thereof, in admixture with a pharmaceutically acceptable diluent or carrier.

There is also provided a method of treatment of one of the aforementioned diseases or conditions which comprises administering a therapeutically effective amount of a compound of formula I, without provisos (e) to (h), or a pharmaceutically acceptable salt thereof, to a person suffering from such a disease or condition.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include: tablets, capsules and dragees: sustained release compositions include those in which the active ingredient is bound to an ion exchange resin which is optionally coated with a diffusion barrier to modify the release properties of the resin.

The enzyme nitric oxide synthetase has a number of isoforms and compounds of formula I, or pharmaceutically acceptable salts thereof, may be screened for nitric oxide synthetase activity by procedures based on those of Bredt and Snyder in *Proc. Natl. Acad. Sci.* (1990) 87, 682–685 and Förstermann et al. (1992) *Eur. J. Pharm.* 225,161–165 as follows. Nitric oxide synthetase converts $^3$H-L-arginine to $^3$H-L-citrulline which can be separated by cation exchange chromatography and quantified by liquid scintillation counting.

Screen A (A) Screen for neuronal nitric oxide synthetase activity

Enzyme was isolated from rat hippocampus or cerebellum. The cerebullum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20,000 g. Residual L-arginine is removed from the supernatant by chromatography through Dowex AG-50W-X8 sodium form and hydrogen form columns successively, and further centrifugation at 1000 g for 30 seconds.

For the assay, 25 μl of the final supernatant is added to each of 12 test tubes containing 25 μl L-arginine solution (of concentration 18 μM $^1$H-L-arginine, 96 nM $^3$H-L-arginine) and either 25 μl of an assay buffer (50 mM HEPES, 1 mM EDTA, 1.5 mM $CaCl_2$, pH 7.4) or 25 μl of test compound in the buffer at 22° C. To each test tube was added 75 μl of complete assay buffer (50 mM HEPES, 1 mM EDTA, 1.5 mM CaCl$_2$, 1 mM DTT, 100 µM NADPH, 10 µg/ml calmodulin, pH 7.4) to initiate the reaction and the reaction is stopped after 10 minutes by addition of 2 ml of a termination buffer (20 mM HEPES, 2 mM EDTA, pH 5.5).

Labelled L-citrulline is separated from labelled L-arginine by chromatography over a Dowex AG-50W-X8 200–400 mesh column. 1 ml of each terminated reaction is added to an individual 1 ml column and the eluant combined with that from two 1 ml distilled water washed and 16 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine, which gives 60% inhibition of nitric oxide synthetase at a concentration of 1 µM, is tested in the assay to verify the procedure.

Screen B (B) Screen for macrophage nitric oxide synthetase activity

Enzyme is prepared after induction, from the cultured murine macrophage cell line J774A-1 (obtained from laboratories of the Imperial Cancer Research Fund). J774A-1 cells are cultured in Dulbecco's Modified Eagles Medium (DMEM) supplemented with 10% foetal bovine serum, 4 mM L-glutamine and antibodies (100 units/ml penicillin G, 100 µg/ml streptomycin & 0.25 µg/ml amphotericin B). Cells are routinely grown in 225 cm$^2$ flasks containing 35 ml medium kept at 37° C. and in a humidified atmosphere containing 5% CO$_2$.

Nitric oxide synthetase is produced by cells in response to interferon-γ (IFNγ) and lipopolysaccharide (LPS). The medium from confluent culture flasks is removed and replaced with 25 ml (per flask) of fresh medium containing 1 µg/ml LPS and 10 units /ml IFNγ. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 µM dithiothreitol and a cocktail of protease inhibitors comprising leupeptin (2 µg/ml), soya bean trypsin inhibitor (10 µg/ml), aprotinin (5 µg/ml) & phenylmethylsulphonyl fluoride (50 µg/ml).

For the assay, 25 µl substrate cocktail (50 mM Tris-HCl (pH 7.5 at 20° C.), 400 µM NADPH, 20 µM flavin adenine dinucleotide, 20 µM flavin mononucleotide, 4 µM tetrahydrobiopterin, 12 µM L-arginine and 0.025 µCi L-[$^3$H] arginine) is added to wells of a 96 well filter plate (0.45 µM pore size) containing 25 µl of a solution of test compound in 50 mM Tris-HCl. The reaction is started by adding 50 µl of cell lysate (prepared as above) and after incubation for 1 hour at room temperature is terminated by addition of 50 µl of an aqueous solution of 3 mM nitroarginine and 21 mM EDTA.

Labelled L-citrulline is separated from labelled L-arginine using Dowex AG-40W. 150 µl of a 25% aqueous slurry of Dowex 50W (Na$^+$form) is added to the assay after which the whole is filtered into 96 well plates. 70 µl of filtrate is sampled and added to wells of 96 well plates containing solid scintillant. After allowing the samples to dry the L-citrulline is quantified by scintillation counting.

In a typical experiment basal activity is 300 dpm per 70 µl sample which is increased to 1900 dpm in the reagent controls. Aminoguanidine, which gives an IC$_{50}$ (50% inhibitory concentration) of 10 µM, is tested as a standard to verify the procedure.

Screen C (C) Screen for endothelial nitric oxide synthetase activity

Enzyme may be isolated from human umbilical vein endothelial cells (HUVECs) by a procedure based on that of Pollock et al (1991) Proc. Nat. Acad. Sci., 88, 10480–10484. HUVECs were purchased from Clonetics Corp (San Diego, Calif., USA) and cultured to confluency. Cells can be maintained to passage 35–40 without significant loss of yield of nitric oxide synthetase. When cells reach confluency, they are resuspended in Dulbecco's phosphate buffered saline, centrifuged at 800 rpm for 10 mins, the cell pellet homogenised in ice-cold 50 mM Tris-HCl, 1 mM EDTA, 10% glycerol, 1 mM phenylmethylsulphonylfluoride, 2 µM leupeptin at pH 4.2. Following centrifugation at 34,000 rpm for 60 mins, the pellet is solubilised in the homogenisation buffer which also contains 20 mM CHAPS. After a 30 min incubation on ice, the suspension is centrifuged at 34,000 rpm for 30 mins. The resulting supernatant is stored at −8020 C. until use.

For the assay, 25 µl of the final supernatant is added to each of 12 test tubes containing 25 µl L-arginine solution (of concentration 12 µM $^1$H-L-arginine, 64 nM $^3$H-L-arginine) and either 25 µl of an assay buffer (50 mM HEPES, 1 mM EDTA, 1.5 mM CaCl$_2$, pH 7.4) of 25 µl of test compound in the buffer at 22° C. To each test tube was added 25 µl of complete assay buffer (50 mM HEPES, 1 mM EDTA, 1.5 mM CaCl$_2$, 1 mM DTT, 100 µM NADPH, 10 µg/ml calmodulin, 12 µM tetrahydrobiopterin, pH 7.4) to initiate the reaction and the reaction is stopped after 10 mins by addition of 2 ml of a termination buffer (20 mM HEPES, 2 mM EDTA, pH 5.5).

Labelled L-citrulline is separated from labelled L-arginine by chromatography over a Dowex AG-50W-X8 200–400 mesh column. 1 ml of each terminated reaction is added to an individual 1 ml column and the eluant combined with that from two 1 ml distilled water washers and 16 ml of scintillation cocktail. The L-citrulline is then quantified by scintillation counting.

In a typical experiment, basal activity is increased by 5,000 dpm/ml of sample above a reagent blank which has an activity of 1500 dpm/ml. A reference standard, N-nitro-L-arginine, which gives 70–90% inhibition of nitric oxide synthetase at a concentration of 1 µM, is tested in the assay to verify the procedure.

Compounds may also be tested in an ex-vivo assay to determine the extent of brain penetration.

Screen D (D) Ex vivo assay for neuronal nitric oxide synthetase activity

Male Sprague-Dawley rats (250–275 g) were dosed intravenously at 10 mg/kg with test compound dissolved in 0.9% saline or with saline alone as control. At a predetermined time (typically 2–24 hours) after treatment, the animals were sacrificed, the cerebellum removed and the supernatant prepared and assayed for nitric oxide synthetase activity as described in Screen A.

As a further confirmatory test, a fraction of the cerebellar supernatant was applied to a 2'–5'-ADP Sepharose column (which binds nitric oxide synthetase) and subsequently eluted with NADPH. The eluant was tested for nitric oxide synthetase activity following the procedure of Screen A.

Compounds that penetrate the rat brain and inhibit neuronal nitric oxide synthetase resulted in reduced nitric oxide synthetase activity in the supernatant preparation and in the eluant from the 2'–5'-ADP Sepharose column.

In the screens for nitric oxide synthetase inhibition activity, compound activity is expressed as IC$_{50}$ (the concentration of drug substance which gives 50% enzyme inhibition in the assay). $IC_{50}$ values for test compounds were initially estimated from the inhibiting activity of 1, 10 and 100 μM solutions of the compounds. Compounds that inhibited the enzyme by at least 50% at 10 μM were retested using more appropriate concentrations so that an $IC_{50}$ could be determined.

In Screen A above (a screen for activity against the neuronal isoform of nitric oxide synthetase), the compound of Example 1 below gave an $IC_{50}$ of less than 10 μM indicating that it is expected to show useful therapeutic activity. In Screens B and C (the screen for activity against the macrophage and endothelial isoforms of nitric oxide synthetase) the compound of Example 1 gave $IC_{50}$ values more than 10 times that obtained in Screen A indicating that it shows desirable selectivity.

The compounds of Examples 2–20, 21(a)–(n), 22(a)–(e), 23(a)–(f), 24–26, 27(a), (b), 28–47 and 49–71 were tested in Screen A and also gave $IC_{50}$ values of less than 10 μM. Example 48 was tested in Screen A and gave an $IC_{50}$ value of less than 100 μM. Example 72 was tested in Screen A and gave 17% inhibition of 10 μM. Thus these compounds are also expected to show useful therapeutic activity.

Compounds of formula I, and pharmaceutically acceptable salts thereof, have the advantage that they are less toxic, more efficacious, more selective, are longer acting, have a broader range of activity, are more potent, produce fewer side effects, are more easily absorbed, or have other useful pharmacological properties than compounds previously known and used in the therapeutic fields mentioned above.

Compounds of formula I, and pharmaceutically acceptable salts thereof, may also have the advantage that they are more selective for the neuronal isoform of nitric oxide synthetase enzyme and are therefore expected to show useful therapeutic activity with a reduced side-effect profile associated with inhibition of the other isoforms.

The invention is illustrated by the following examples:

EXAMPLE 1

N-(4-(2-((phenylmethyl)amino)ethyl)phenyl)-2-thiopenecarboximidamide (a) N-(2-(4-nitrophenyl)ethyl)trifluoroacetamide To a stirred solution of 4-nitrophenethylamine hydrochloride (1.84 g, 9.10 mmol) and triethylamine (3.03 ml, 2.170 mmol) in methanol (12 ml) was added trifluoroacetic anhydride (1.51 ml, 10.66 mmol) dropwise. After stirring for 1 minute, the solvent was removed at reduced pressure and the remaining residue was mixed with water and extracted with methylene chloride (3×20 ml). The combined extracts were washed with water, dried over magnesium sulfate, filtered, and concentrated to yield a solid which was recrystallized from methylene chloride/hexane to give N-(2-(4-nitrophenyl)ethyl)trifluoroacetamide as a white solid: 1.92 g (80% yield); m.p. 103–104° C.

(b) N-(2-(4-nitrophenyl)ethyl)-N-(phenylmethyl)trifluoroacetamide

To a stirred solution of the product of step (a) (0.89 g, 3.40 mmol) in THF (5 ml) at 0° C. was added NaH (60%, 0.18 g, 4.42 mmol) followed by benzyl bromide (0.50 ml, 4.10 mmol). The mixture was stirred at room temperature for 6 h, quenched with water, and extracted with ethyl acetate (3×30 ml). The combined extracts were washed with water, dried over magnesium sulfate, filtered, concentrated, and chromatographed over silica gel (18% ethylacetate/hexane) to give N(2-(4-nitrophenyl)ethyl)-N-phenylmethyl)trifluoroacetamide as a colourless oil: (0.52 g, 44%); M.S. $(M+H)^+$=353.

(c) N-(2-(4-aminophenyl)ethyl)-N-phenylmethyl)trifluoroacetamide

To a stirred solution of the product of step (b) (0.52 g, 1.48 mmol) in THF/MeOH (100 ml, 1:1) was added a catalytic amount of 10% Pd/C. The mixture was hydrogenated at 50 psi for 1 hr, filtered through celite, and concentrated to give N(2-(4-aminophenyl)ethyl)-N-(phenylmethyl) trifluoroacetamide which was homogeneous by TLC and used immediately in the next reaction.

(d) S-methyl-2-thiophenethiocarboximide hydroiodide

A solution of 2-thiophenecarboxthioamide (Maybridge Chemical) (11.1 g) in 60 ml of acetone was treated with iodomethane (13.4 g). After 6 hrs at 22° C., the resulting yellow solids were collected by filtration, washed twice with 25 ml of acetone and dried to provide 18.45 g of S-methyl-2-thiophenethiocarboximide hydroiodide, m.p. 195° C. (dec).

(e) N-(4-(2-((phenylmethyl)amino)ethyl)phenyl)-2-thiophenecarboximidamide

To a solution of N(2-(4-aminophenyl)ethyl)-N-(phenylmethyl)trifluoroacetamide (48 g, 1.48 mmol) in isopropanol (6 ml) was added S-methyl-2-thiophenethiocarboximide hydroiodide (0.42 g, 1.48 mmol). The mixture was stirred for 4 hr, diluted with methanol (5 ml) and 2N NaOH (6 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, and concentrated to give a solid which was recrystallized (ethyl acetate/hexane) to yield N-(4-(2-((phenylmethyl)amino)ethyl)phenyl)-2-thiophenecarboximidamide as a white solid: (0.17 g, 34%); m.p. 116–118° C.

EXAMPLE 2

N-(4-(1-((phenylmethyl)amino)methyl)phenyl)-2-thiophenecarboximidamide (a) N-((4-nitrophenyl)methyl)trifluoroacetamide To a stirred solution of 4-nitrobenzylamine hydrochloride (4.06 g, 21.5 mmol) and triethylamine (6.60 ml, 47.4 mmol) in methylene chloride (30 ml) was added trifluoroacetic anhydride (3.34 ml, 23.7 mmol) dropwise. After stirring for 1 minute, water was added and the layers separated. The aqueous layer was further extracted with methylene chloride (3×20 ml) and the combined extracts were washed with water, dried over magnesium sulfate, filtered, and concentrated to yield a solid which was recrystallized from methylene chloride/hexane to give N-((4-nitrophenyl)methyl)trifluoroacetamide as a white solid: 3.9 g (73% yield); m.p. 97–98° C.

(b) N-((4-nitrophenyl)methyl)-N-(phenylmethyl)trifluoroacetamide

To a stirred solution of the product of step (a) (1.0 g, 4.03 mmol) in THF (10 ml) at 0° C. was added NaH (60%, 0.21 g, 5.24 mmol) followed by benzyl bromide (0.72 ml, 4.84 mmol). The mixture was stirred at room temperature for 12 h, quenched with water, and extracted with ethyl acetate (3×30 ml). The combined extracts were washed with water, dried over magnesium sulfate, filtered, concentrated, and chromatographed over silica gel (16% ethylacetate/hexane) to give N-((4-nitrophenyl)methyl)-N-(phenylmethyl)trifluoroacetamide as a colorless oil: (0.50 g, 40%); M.S. $(M+H)^+$32 339.

(c) N((4-aminophenyl)methyl)-N-(phenylmethyl)trifluoroacetamide

To a stirred solution of the product of step (b) (1.76 g, 5.16 mmol) in THF/MeOH (100 ml, 1:1) was added a catalytic amount of 10% Pd/C. The mixture was hydrogenated at 50 psi for 0.5 hr, filtered through celite, and concentrated to give N((4-aminophenyl)methyl)-N-(phenylmethyl) trifluoroacetamide which was homogeneous by TLC and used immediately in the next reaction.

(d) N(-4-(1-((phenylmethyl)amino)methyl)phenyl)-2-thiophenecarboximidamide

To a solution of the product of step (c) (1.60 g, 5.16 mmol) in isopropanol (6 ml) was added S-methyl-2-thiophenethiocarboximide hydroiodide (the product of Example 1, step (d)) (1.47 g, 5.16 mmol). The mixture was stirred for 24 hr at 40 ° C., diluted with methanol (5 ml) and 2N NaOH (15 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, concentrated and chromatographed over silica gel (8% methanol/methylene chloride) to give a solid which was recrystallized (ethyl acetate/hexane) to yield N-(4-(1-((phenylmethyl)amino) methyl)phenyl)-2-thiophenecarboximidamide as a whie solid: (60 mg, 4%); m.p. 73–74° C.

EXAMPLE 3

N-(4-1-((phenethyl)amino)methyl)phenyl)-2-thiophenecarboximidamide (a) N-(2-phenylethyl)trifluoroacetamide To a stirred solution of phenethylamine (4.91 g, 40.5 mmol) and triethylamine (6.50 ml, 46.6 mmol) in methylene chloride (30 ml) was added trifluoroacetic anhydride (6.3 ml, 44.6 mmol) dropwise. After stirring for 1 minute, water was added and the layers separated. The aqueous layer was further extracted with methylene chloride (3×40 ml) and the combined extracts were washed with water, dried over magnesium sulfate, filtered, and concentrated to yield a solid which was recrystallized from methylene chloride/hexane to give N-(2-phenylethyl)trifluoroacetamide as a white solid: 6.0 g 69% yield); m.p. 50–52 ° C.

(b) N-(2-phenylethyl)-N-((4-nitrophenyl)methyl) trifluoroacetamide

To a stirred solution of the product of step (a) (2.0 g, 9.26 mmol) in THF (10 ml) at 0° C. was added NaH (60%, 0.37 g, 9.26 mmol) followed by 4-nitrobenzyl bromide (1.0 g, 4.63 mmol). The mixture was stirred at room temperature for 1 hr, quenched with water, and extracted with ethyl acetate (3×30 ml). The combined extracts were washed with water, dried over magnesium sulfate, filtered, concentrated, and chromatographed over silica gel (16% ethylacetate/hexane) to give N-2-phenylethyl)-N-((4-nitrophenyl)methyl) trifluoroacetamide as a colorless oil: (1.60 g, 98%); M.S. (M+H)$^+$=353.

(c) N-(2-phenylethyl)-N-((4-aminophenyl)methyl) trifluoroacetamide

To a stirred solution of the product (b) (1.60 g, 4.54 mmol) in THF/MeOH (100 ml, 1:1) was added a catalytic amount of 10% Pd/C. The mixture was hydrogenated at 50 psi for 0.75 hr, filtered through celite, and concentrated to give N-(2-phenylethyl)-N-((4-aminophenyl)methyl) trifluoroacetamide which was homogeneous by TLC and used immediately in the next reaction.

(d) N-(4-(1-((2-phenylethyl)amino)methyl)phenyl)2-thiophenecarboximidamide

To a solution of the product of step (c) (1.47 g, 4.54 mmol) in iospropanol (5 ml) was added S-methyl-2-thiophenethiocarboximide hydroiodide (the product of Example 1, step (d)) (1.30 g, 4.54 mmol). The mixture was stirred for 24 hr at 40° C., diluted with methanol (5 ml) and 2N NaOH (10 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, concentrated and chromatographed over silica gel (10% methanol/methylene chloride) to give a solid which was recrystallized (ethyl acetate/hexane) to yield N-(4-(1-((2-phenylethyl)amino) methyl)phenyl)-2-thiophenecarboximidamide as a white solid: (20 mg, 2%); M.S. (M+H)$^+$=336.

EXAMPLE 4

N-(4-(2-((2-chlorophenylmethyl)amino)ethyl) phenyl)-2-thiophenecarboximidamide (a) N-(4-nitrophenyl)ethyl)-N-((2-chlorophenyl)methyl) trifluoroacetamide To a stirred solution of N-(2-(4-nitrophenyl)ethyl) trifluoroacetamide (the product of Example 1 step (a)) (2.0 g, 7.63 mmol) and a catalytic amount of 15-crown-5 in THF (10 ml) at 0° C. was added NaH (60%, 0.18 g, 4.42 mmol) followed by 2 -chlorobenzyl bromide (1.49 ml, 11.45 mmol). The mixture was stirred at room temperature for 2 hr, quenched with water, and extracted with ethyl acetate (3×30 ml). The combined extracts were washed with water, dried over magnesium sulfate, filtered, concentrated, and chromatographed over silica gel (18% ethylacetate/hexane) to give N-(2-(4-nitrophenyl)ethyl)-N-((2-chlorophenyl) methyl)trifluoroacetamide as a colourless oil: (2.31 g, 78%); M.S. (M+H)$^+$=353.

(b) N-(2-(4-aminophenyl)ethyl)-N-((2-chlorophenyl) methyl)trifluoroacetamide

To a stirred solution of the product of step (a) (2.31 g, 5.96 mmol) in THF/MeOH (100 ml, 1:1) was added a catalytic amount of 10% Pd/C. The mixture was hydrogenated at 50 psi for 1 hr, filtered through celite, and concentrated to give N-(2-(4-aminophenyl)ethyl)-N-((2-chlorophenyl)methyl) trifluoroacetamide which was homogeneous by TLC and used immediately in the next reaction.

(c) N-(4-(2-((2-chlorophenylmethyl)amino)ethyl)phenyl)-2-thiophenecarboximidamide To a solution of the product of step (b) (2.1 g, 5.96 mmol) in isopropanol (10 ml) was added S-methyl-2-thiophenethiocarboximide hydroiodide (the product of Example 1, step (d)) (1.7 g, 5.96 mmol). The mixture was stirred for 24 h, diluted with methanol (10 ml) and 2 N NaOH (6 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, concentrated and chromatographed over silica gel (10% methanol/methylene chloride) to give a solid which was recrystallized (methylene chloride/hexane) to yield N-(4-(2-((2-chlorophenylmethyl) amino)ethyl)phenyl)-2-thiophenecarboximidamide as a white solid: (0.21 g, 10%); m.p. 81–82° C.

EXAMPLE 5

N-(4-(2-((3-fluorophenylmethyl)amino)ethyl) phenyl)-2-thiophenecarboximidamide (a) N((3-fluorophenyl)methyl)-N-(2-(4-nitrophenyl)ethyl) trifluoroacetamide To a stirred solution of N-(2-(4-nitrophenyl)ethyl) trifluoroacetamide (the product of Example 1 step (a)) (1.5 g, 5.75 mmol) and a catalytic amount of 15-crown-5 in THF (10 ml) at 0° C. was added NaH (60%, 0.25 g, 6.34 mmol) followed by 3-fluorobenzyl bromide (1.40 ml, 11.45 mmol). The mixture was stirred at room temperature for 4 hr, quenched with water, and extracted with ethyl acetate (3×30 ml). The combined extracts were washed with water, dried over magnesium sulfate, filtered, concentrated, and chromatographed over silica gel (18% ethyl acetate/hexane) to give N-((3-fluorophenyl)methyl)-N-(2-(4-nitrophenyl) ethyl)trifluoroacetamide as a colourless oil: (1.63 g, 77%); M.S. (M+H)$^+$=371.

(b) N-(2-(4-aminophenyl)ethyl)-N-((3-fluorophenyl) methyl)trifluoroacetamide

To a stirred solution of the product of step (a) (1.63 g, 4.40 mmol) in THF/MeOH (100 ml, 1:1) was added a catalytic amount of 10% Pd/C. The mixture was hydrogenated at 50 psi for 1 hr, filtered through celite, and concentrated to give N-(2-(4-aminophenyl)ethyl)-N-((3-fluorophenyl)methyl) trifluoroacetamide which was homogeneous by TLC and used immediately in the next reaction.

(c) N-(4-(2-((3-fluorophenylmethyl)amino)ethyl)phenyl)-2-thiophenecarboximidamide To a solution of the product of step (b) (1.5 g, 4.40 mmol) in methanol (10 ml) was added S-methyl-2-thiophenethiocarboximide hydroiodide (the product of Example 1, step (d)) (1.3 g, 4.40 mmol). The mixture was stirred for 2 hr, diluted with methanol (5 ml) and 2 N NaOH (8 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, and concentrated to give a solid which was recrystallized, (methylene chloride/hexane) to yield N-(4-(2-(((3-fluorophenyl)methyl)amino)ethyl) phenyl)-2-thiophenecarboximidamide as a white solid: (0.14 g, 8%); m.p. 130–131° C.

EXAMPLE 6

N-(4-(2-(((2-methylphenyl)methyl)amino)ethyl) phenyl)-2-thiophenecarboximidamide (a) N-((2-methylphenyl)methyl)-N-(2-(4-nitrophenyl)ethyl) trifluoroacetamide To a stirred solution of N-(2-(4-nitrophenyl)ethyl) trifluoroacetamide (the product of Example 1 step (a)) (1.5 g, 5.75 mmol) and a catalytic amount of 15-crown-5 in THF (10 ml) at 0° C. was added NaH (60%, 0.25 g, 6.34 mmol) followed by 2-methylbenzyl bromide (1.53 ml, 11.45 mmol). The mixture was stirred at room temperature for 2 hr, quenched with water, and extracted with ethyl acetate (3×30 ml). The combined extracts were washed with water, dried over magnesium sulfate, filtered, concentrated, and chromatographed over silica gel (18% ethylacetate/hexane) to give N-((2-methylphenyl)methyl)-N-(2-(4-nitrophenyl) ethyl)trifluoroacetamide as a colorless oil: (1.76 g, 84%); M.S. (M+H)$^+$=367.

(b) N-(2-(4-aminophenyl)ethyl)-N-((2-methylphenyl) methyl)-trifluoroacetamide

To a stirred solution of the product of step (a) (1.76 g, 4.82 mmol) in THF/MeOH (100 ml, 1:1) was added a catalytic amount of 10% Pd/C. The mixture was hydrogenated at 50 psi for 1 hr, filtered through celite, and concentrated to give N-(2-(4-aminophenyl)ethyl)-N-((2-methylphenyl)methyl)-trifluoroacetamide which was homogeneous by TLC and used immediately in the next reaction.

(c) N-(4-(2-(((2-methylphenyl)methyl)amino)ethyl) phenyl)-2-thiophenecarboximidamide To a solution of the product of step (b) (1.62 g, 4.82 mmol) in methanol (10 ml) was added S-methyl-2-thiophenethiocarboximide hydroiodide (the product of Example 1, step (d)) (1.37 g, 4.82 mmol). The mixture was stirred for 2 hr, diluted with 2 N NaOH (8 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, and concentrated to give a solid which was recrystallized (methylene chloride/hexane) to yield N-(4-(2-(((2-methylphenyl)methyl)amino)ethyl)phenyl)-2-thiophenecarboximidamide as a white solid: (0.46 g, 28%); m.p. 105–106° C.

EXAMPLE 7

N-(4-(2-(methylamino)ethyl)phenyl)-2-thiophenecarboximidamide (a) N-methyl-N-(2-(4-nitrophenyl)ethyl)trifluoroacetamide To a stirred solution of N-(2-(4-nitrophenyl)ethyl) trifluoroacetamide (the product of Example 1 step (a)) (1.5 g, 5.75 mmol) and a catalytic amount of 15-crown-5 in THF (10 ml) at 0° C. was added NaH (60%, 0.25 g, 6.34 mmol) followed by methyliodide (0.71 ml, 11.45 mmol). The mixture was stirred at room temperature for 4 hr, quenched with water, and extracted with ethyl acetate (3×30ml). The combined extracts were washed with water, dried over magnesium sulfate, filtered, and concentrated to yield. N-methyl-N-(2-(4-nitrophenyl)ethyl)trifluoroacetamide a colorless oil: (1.40 g, 88%); M.S. (M+H)$^+$=277.

(b) N-methyl-N-(2-(4-aminophenyl)ethyl) trifluoroacetamide

To a stirred solution of the product of step (a) (1.45 g, 5.25 mmol) in THF/MeOH (100 ml, 1:1) was added a catalytic amount of 10% Pd/C. The mixture was hydrogenated at 50 psi for 1 hr, filtered through celite, and concentrated to give N-methyl-N-(2-(4-aminophenyl)ethyl)trifluoroacetamide which was homogeneous by TLC and used immediately in the next reaction.

(c) N-(4-(2-(methylamino)ethyl)phenyl)-2-thiophenecarboximidamide

To a solution of the product of step (b) (1.32 g, 5.37 mmol) in methanol (10 ml) was added S-methyl-2-thiophenethiocarboximide hydroiodide (the product of Example 1, step (d)) (1.53 g, 5.37 mmol). The mixture was stirred for 2 hr, diluted with 2 N NaOH (8 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, and concentrated to give a solid which was recrystallized (methylene chloride/hexane) to yield N-(4-(2-((2-methylphenylmethyl)amino)ethyl)phenyl)-2-thiophenecarboximidamide as a white solid: (0.43 g, 31%); M.S. (M+H)$^+$=260.

EXAMPLE 8

N-(4-(2-aminoethyl)phenyl)-2-thiophenecarboximidamide (a) N-(2-(4-aminophenyl)ethyl)trifluoroacetamide To a stirred solution of N-(2-(4-nitrophenyl)ethyl) trifluoroacetamide (the product of Example 1 step (a)) (1.00 g, 3.81 mmol) in THF/MeOH (100 ml, 1:1) was added a catalytic amount of 10% Pd/C. The mixture was hydrogenated at 50 psi for 1 hr, filtered through celite, and concentrated to give N-(2-(4-aminophenyl)ethyl)trifluoroacetamide which was homogeneous by TLC and used immediately in the next reaction.

(c) N-(4-(2-aminoethyl)phenyl)-2-thiophenecarboximidamide

To a solution of the product of step (a) (0.88 g, 3.81 mmol) in methanol (10 ml) was added S-methyl-2-thiophenethiocarboximide hydroiodide (the product of Example 1, step (d)) (1.09 g, 3.81 mmol). The mixture was stirred for 12 hr, diluted with 2 N NaOH (8 ml) and heated to 70° C. for 1 hr. The solvents were removed at reduced pressure, and the residue was dumped into water and extracted with ethyl acetate (3×30 ml). The combined extracts were washed with water, dried over magnesium sulfate, filtered, and concentrated to give a solid which was recrystallized (ethyl acetate/methanol) to yield N-(4-(2-aminoethyl)phenyl)-2-thiophenecarboximidamide as a white solid: (70 m g, 8%); m.p. 134–137° C.

EXAMPLE 9

N-((4-morpholinylmethyl)phenyl)-2-thiophenecarboximidamide (a) 4-(4-Nitrobenzyl)-morpholine To a stirred solution of (2.00 g, 0.0093 mmol) 4-nitrobenzyl bromide (Aldrich) and (0.736 g; 0.011 mol) potassium carbonate anhydrous (Aldrich) in 20.0 ml DMF was added (0.796 ml; 0.0093 mol) morpholine. The reaction was heated to 50° C. and stirred for 30 minutes, after which time and additional 0.1 equivalents of morpholine and potassium carbonate were added. After 30 minutes the reaction mixture was quenched with 100 ml water and extracted with (4×100 ml) ethyl acetate. The organic layers were collected and dried over magnesium sulfate and the solvent evaporated. The resulting solids were recrystallized from ethyl acetate and hexane to leave 1.90 g of 4-(4-nitrobenzyl)-morpholine.

(b) (4-morpholinylmethyl)aniline

A (1.00 g; 0.0045 mol) sample of 4-(4-nitrobenzyl)-morpholine was dissolved in 25 ml each THF and methanol in a pressure bottle. A catalytic amount of 10% palladium on carbon was added and the reaction hydrogenated. When hydrogen uptake had ceased, the catalyst was removed by filtration and the solvents evaporated. The solids were dissolved in 30 ml each ethyl acetate and water, and 30 ml 2N sodium hydroxide. The aqueous layer was extracted with (4×75 ml) ethyl acetate. The organic layers were collected, dried, over magnesium sulfate, and the solvent evaporated under vacuum. The resulting solids were recrystallized from ethyl acetate and hexane to leave 0.68 g of (4-morpholinylmethyl)aniline.

(c) N-((4-morpholinylmethyl)phenyl)-2-thiophenecarboximidamide

To a stirred solution of the product of step (b) (0.68 g; 0.0035 mmol) and 15.0 ml isopropyl alcohol was added S-methyl-2-thiophenethiocarboximide hydroiodide (the product of Example 1, step (d)) (0.99 g; 0.0035 mmol). The mixture was stirred at 35C. To this mixture was added 10.0 ml methanol along with 2M hydrochloric acid in isopropyl alcohol added dropwise until all of the reactants were in solution. The reaction was allowed to stir for 48 hours. The reaction was then diluted in 50 ml saturated sodium chloride and extracted with (3×75 mL) ethyl acetate. The organic layers were collected, dried over magnesium sulfate, and the solvent evaporated. The crude product was separated on a silica gel column eluted with 10% methanol in methylene chloride. The solvent was evaporated and the crude solid recrystallized twice from ethyl acetate and hexane to leave 60 mg of N-((4-morpholinylmethyl)phenyl)-2-thiophenecarboximidamide, m.p.=148–150° C.

EXAMPLE 10

N-(3-(((phenylmethyl)amino)methyl)phenyl)-2-thiophenecarboximidamide bisoxalate (a) N-(3-nitrobenzyl)benzamide To a solution of 3-nitrobenzyl amine hydrochloride (2.45 g, 0.013 mol) in a solution of 50 ml of methylene chloride and 50 ml of half saturated aqueous potassium carbonate at 0° C. was added dropwise a solution of benzoyl chloride (2.1 g, 0.0149 mol) in 10 ml of methylene chloride. After addition was complete, the reaction mixture was stirred for 2 h at 0° C. and was then allowed to warm to ambience overnight. The organic layer was separated and was washed successively with dilute hydrochloric acid and water. The dried (MgSO$_4$) organic phase was concentrated in vacuo to give 2.92 g (88%) of the title product, m.p. 136–8° C.

(b) N-benzyl-2,2,2-trifluoro-N-(3-nitrobenzyl)acetamide

To a solution of the product of step (a) (2.85 g, 11.1 mmol) in 50 ml of anhydrous tetrahydrofuran at 0° C. under nitrogen was added 18.6 ml of a 1.0 M borane in THF solution (18.6 mmol). The reaction mixture was then heated to reflux for 5.5 h. The solution was allowed to cool overnight and was then quenched by the successive addition of 2 ml of methanol and 10 ml of 6 M hydrochloric acid. The reaction mixture was again heated to reflux for 1 h. Upon cooling to ambience, the reaction mixture was basified and extracted into ether. The dried (MgSO$_4$) was concentrated to afford an oil. This oil was chromatographed on silica gel using methylene chloride as eluent to give 1.95 g (72%) of benzyl-3-(nitrobenzyl)amine as an oil. To a solution of the crude benzyl-3-(nitrobenzyl)amine (1.95 g, 8.05 mmol) and triethylamine (2.6 Ml, 18 mmol) in 20 ml of methylene chloride under nitrogen at 0° C., was added dropwise trifluoroacetic anhydride (3.4 g, 16 mmol). The reaction mixture was stirred for 10 minutes before pouring into water. The organic layer was separated and dried over magnesium sulfate. The solution was filtered and concentrated to give an oil. Chromatography on silica gel, using 20% ethyl acetate in hexanes as eluent afforded 1.46 g (54%) of the product as an oil, mass spectrum m/e 339 (100%, M+H).

(c) N-(3-aminobenzyl)-N-benzyl-2,2,2-trifluoroacetamide

To a solution of the product of step (b) (1.21 g, 3.58 mmol) dissolved in a solution of 100 ml of methanol was added 20 ml of a saturated solution of hydrogen chloride in isopropanol and 0.1 g of 5% Pd/C. The resulting solution was hydrogenated at 50 psi for one hour. The catalyst was removed by filtration and the filtrate was concentrated in vacuo solid. Trituration of this solid with ether afforded 1.15 g (93%) of the title compound as the hydrochloride salt, m.p. 169–74° C.

(d) N-(3-(((phenylmethyl)amino)methyl)phenyl)-2-thiophenecarboximidamide

To a solution of 0.25 g (0.94 mmol) of S-methyl 2-thiophenethiocarboximide hydroiodide (the product of Example 1, step (d)) in 4 ml of isopropanol was added 0.41 g (1.3 mmol) of N-(3-aminobenzyl)-N-benzyl-2,2,2-trifluoroacetamide (prepared by taking the hydrochloride salt and neutralizing with 2.5 m NaOH and extracting into methylene chloride). The reaction mixture was stirred for 5 h. A solution (2 ml) of 2.5 M sodium hydroxide and about 5 drops of methanol was added and the resulting solution was heated at reflux for 1 h. The solution was concentrated and the product was extracted into ethyl acetate. The solution was dried and concentrated to give a solid. This solid was dissolved in ethanol and oxalic acid dihydrate (0.16 g, 1.3 mmol) was added. The resulting salt was collected and dried to give 0.26 g (55%) of the title compound as the bis oxalate salt mp 178–183° C.

EXAMPLE 11

An alternative synthesis for the compound of Example 2.

N-(4-(((phenylmethyl)amino)methyl)phenyl)-2-thiophenecarboximidamide (a) N-(4-nitrobenzyl)benzamide)

This compound was prepared following the method of Example 10, step (a). From 4-nitrobenzyl amine (2.45 g, 0.013 mol) and benzoyl chloride (2.1 g, 0.0149 mol) was isolated 2.56 g (77%) of the title product, m.p. 150–3° C.

(b) N-benzyl-2,2,2-trifluoro-N-(4-nitrobenzyl)acetamide

This compound benzyl-(4-nitrobenzyl)amine was prepared using the method described in Example 10, step (b) for the preparation of benzyl-3-(nitrobenzyl)amine. From 2.49 g (9.36 mmol) of N-(4-nitrobenzyl)-benzamide and 18.6 ml of 1.0 M borane in THF was obtained 3.12 g of the crude benzyl-(4-nitrobenzyl)amine, which was used without further purification. This crude product was mixed with 4.3 ml of triethylamine in 40 ml of methylene chloride at 0° C. under nitrogen. To this solution was added dropwise 3.6 ml of trifluoroacetic anhydride. The solution was stirred for 10 minutes and was poured into water and separated. The dried organic phase was dried ($MgSO_4$) and concentrated to give 3.1 g (94%) of the title compound as an oil.

(c) N-(4-aminobenzyl)-N-benzyl-2,2,2-trifluoroacetamide

This compound was prepared using the method described in Example 10, step (c) for the preparation of N-(3-aminobenzyl)-N-benzyl-2,2,2-trifluoroacetamide. From N-benzyl-2,2,2-trifluoro-N-(4-nitrobenzyl)acetamide (3.1 g, 9.2 mmol) was obtained 2.46 g (78%) of the title compound as the hydrochloride salt following hydrogenation. Recrystallization from isopropanol and ether gave 1.74 g of pure material, m.p. 115–9° C.

(d) N-(4-(((phenylmethyl)amino)methyl)phenyl)-2-thiophenecarboximidamide

From 0.60 g (1.9 mmol) of the free base of N-(4-aminobenzyl)-N-benzyl-2,2,2-trifluoroacetamide and 0.42 g (1.6 mmol) of S-methyl 2-thiophenethiocarboximide (prepared by taking the hydrochloride salt produced by following a method analogous to that of Example 1, step (d), and neutralizing with 2.5 m NaOH and extracting into methylene chloride) in 4 ml of isopropanol. The reaction mixture was stirred for 5 h. A solution (2 ml) of 2.5 M sodium hydroxide and about 5 drops of methanol was added and the resulting solution was heated at reflux for 1 h. The solution was concentrated and the product was extracted into ethyl acetate. The solution was dried and concentrated to give a solid. This was converted to the bis oxalate in isopropanol and then recrystallized from 95% ethanol to give 110 mg (10%) of the title compound, mp 209–13° C.

EXAMPLE 12

The following compounds were prepared following the method of Example 1:

(a) N-(4-(2-(((2.6-dichlorophenyl)methyl)amino)ethyl) phenyl)-2-thiophenecarboximidamide m.p. 104–105° C.
(b) N-(4-(2-(((2-bromophenyl)methyl)amino)ethyl)phenyl)-2-thiophenecarboximidamide m.p. 81–82° C.
(c) N-(3-(2-((Phenylmethyl)amino)ethyl)phenyl)-3-thiophenecarboximidamide dihydrochloride, m.p. 145–147° C.
(d) N-(4-(2-((2,6-dichlorophenylmethyl)amino)ethyl) phenyl)-3-thiophenecarboximidamide free base, m.p. 109–110° C.
(e) N-(4-(2-aminoethyl)phenyl)-3-thiophenecarboximidamide dihydrobromide m.p. 158–170 dec
(f) N-(4-(2-((2,6-dichlorophenylmethyl)amino)ethyl) phenyl)-2-furanocarboximidamide free base, m.p. 101–104° C.
(g) N-(3-(3-(1-pyrolidinyl)propyl)phenyl)-2-thiophenecarboximidamide free base, m.p. 110–111° C.
(h) N-(4-(2-aminoethyl)phenyl)-2-furocarboximidamide dioxalate, m.p. 162° C. dec

EXAMPLE 13

The following compounds were prepared following the method of Example 9:

(a) N-(4-((1-piperidinyl)methyl)phenyl)-2-thiophenecarboximidamide dihydrobromide m.p. 277–278° C.
(b) N-(4-((1-pyrrolidinyl)methyl)phenyl)-2-thiophenecarboximidamide dihydrobromide m.p. 248–250° C.

EXAMPLE 14

The following compound was prepared following the method of Example 10: N-(3-(((phenylmethyl)amino) methyl)phenyl)-2-thiophenecarboximidamide dimaleate m.p. 171–173° C.

EXAMPLE 15

The following compound was prepared following the general method of Example 1 starting at step (e) by reacting S-methyl-2-thiophenecarboximide hydroiodide with 3-(methylamino)phenylamine.

N-(3-((amino)methyl)phenyl)-2-thiophenecarboximidamide dimaleate m.p. 145–148° C.

EXAMPLE 16

The following compound was prepared following the method of Example 10 N-(3-(2-((phenylmethyl)amino) ethyl)phenyl)-2-thiophenecarboxamidine Dioxalate m.p. 132–134° C.

EXAMPLE 17

N-(3-(2-(Ethylamino)ethyl)phenyl)-2-thiophenecarboximidamide (a) (3-Nitrophenyl)acetyl chloride A stirred solution of 3-nitrophenylacetic acid (10.0 g, 55.2 mmol) in thionyl chloride (100 ml, 1.37 mol) was heated at reflux for 2 hours, then concentrated to yield 11.1 g of (3-nitrophenyl)acetyl chloride as a tan solid.

(b) N-Ethyl-2-(3-nitrophenyl)acetamide

To a stirred solution of 70 wt % ethylamine in water (35 ml) cooled on an ice bath was added in one portion (3-nitrophenyl)acetyl chloride (3 g, 15.0 mmol). Resulting mixture was warmed to achieve a clear solution, allowed to cool. Resulting precipitate was filtered to yield N-ethyl-2-(3-nitrophenyl)acetamide as a yellow solid: (2.2 g, 71%); m.p. 115–117° C.

(c) Ethyl-(2-(3-nitrophenyl)ethyl)amine hydrochloride

To a stirred solution of the product of step (b) (2.2 g, 10.6 mmol) in tetrahydrofuran (50 ml) under nitrogen, was added dropwise 1.0M borane-tetrahydrofuran (42 ml, 42 mmol). Reaction was heated at reflux for 1.5 hours, cooled on ice bath, then aqueous 6N HCl (75 ml) added dropwise. The resulting mixture was refluxed for 1 hour, basified to pH 11 with 20% aqueous sodium hydroxide, extracted twice with ether. Combined extracts were dried over magnesium sulfate, filtered, concentrated. The hydrochloride salt of the crude was made from isopropanol and ethyl acetate to yield ethyl-(2-(3-nitrophenyl)ethyl)amine hydrochloride as a light yellow solid: (1.7 g, 70%); m.p. 186–188° C.

(d) 3-(2-Ethylamino-ethyl)phenylamine hydrochloride

To a solution of the product of step (c) (1.7 g, 7.0 mmol) in methanol (30 ml) was added a catalytic amount of 10% palladium on carbon. The mixture was hydrogenated at 50 psi for 30 minutes, filtered through celite, concentrated to yield 3-(2-ethylamino-ethyl)phenylamine hydrochloride as an off-white solid: (1.4 g, 100%); m.p. 192–194° C.

(e) N-(3-(2-(Ethylamino)ethyl)phenyl)-2-thiophenecarboximidamide dihydrobromide

To a solution of the product of step (d) (1.4 g, 7.0 mmol) in isopropanol (20 ml) and dimethylformamide (20 ml) was added S-methyl-2-thiophenethiocarboximide hydroiodide (2.5 g, 8.8 mmol). The mixture was stirred for 16 hours, diluted with 20% aqueous sodium hydroxide, and extracted twice with ethyl acetate. The combined extracts were washed twice with water, dried over magnesium sulfate, filtered, and concentrated to give 2.7 g of an oil. The dihydrobromide salt was made from isopropanol and ethyl acetate, recrystallized from isopropanol, methanol, and ethyl acetate to yield N-(3-(2-(ethylamino)ethyl)-phenyl)-2-thiophenecarboximidamide dihydrobromide as a tan solid: (1.72 g, 49%); m.p. 192–194° C. (dec).

EXAMPLE 18

N-(3-(3-((Phenylethyl)amino)propyl)phenyl)-2-thiophenecarboximidamide Dioxalate (a) 3-(3-(Phenylethylamino-propyl)phenylamine dihydrochloride This was prepared following a method analogous to that of Example 17, steps (a)–(d).

(b) N-(3-(3-((Phenylethyl)amino)propyl)phenyl)-2-thiophenecarboximidamide dioxalate To a solution of the product step (a) (3.0 g, 9.17 mmol) and S-methyl-2-thiophenethiocarboximide hydroiodide (3.3 g, 11.5 mmol) in isopropanol (25 ml) and dimethylformamide (25 ml) was added pyridine (0.74 ml, 9.17 mmol) in one portion. The mixture was stirred for 16 hours, diluted with 20% aqueous sodium hydroxide, and extracted twice with ethyl acetate. The combined extracts were washed twice with water, dried over magnesium sulfate, filtered, and concentrated. The dioxalate salt of the crude was made from ethanol and ether, recrystallized from ethanol to yield N-(3-(3-((phenylethyl)amino)propyl)phenyl)-2-thiophenecarboximidamide dioxalate as the white solid: (2.3 g, 44%); m.p. 102–105° C.

EXAMPLE 19

N-(3-(2-(((2-Bromophenyl)methyl)amino)ethyl) phenyl)-2-thiophenecarboximidamide (a) N-(2-Bromobenzyl)-2-(3-nitrophenyl)acetamide This was prepared following a method analogous to that of Example 17, steps (a)–(b).

(b) N-(2-Bromobenzyl)-2-(3-aminophenyl)acetamide

To a solution of the product of step (a) (5.45 g, 15.6 mmol) in 85% glacial acetic acid (400 ml) was added in one portion the zinc dust (10.2 g, 156 mmol). Reaction was stirred for 30 minutes, filtered, and concentrated. The residue was partitioned with 20% aqueous sodium hydroxide and dichloromethane, the organic layer was dried over magnesium sulfate, filtered, concentrated to yield N-(2-bromobenzyl)-2-(3-aminophenyl)acetamide as a white solid: (4.7 g, 94%); m.p. 110–112° C.

(c) 3-(2-(2-Bromobenzylamino)ethyl)phenylamine dihydrochloride

This was prepared following a method analogous to that of Example 17, step (c).

(d) N-(3-(2-(((2-Bromophenyl)methyl)amino)ethyl) phenyl)-2-thiophenecarboximidamide dioxalate This was prepared following a method analogous to that of Example 18, step (b). m.p. 175–8° C. (dec)

EXAMPLE 20

N-(3-(2-(Phenylamino)ethyl)phenyl)-2-thiophenecarboximidamide dihydrobromide (a) (2-(3-Nitrophenyl)ethyl)phenylamine This was prepared following a process analogous to that of Example 17, steps (a)–(c).

(b) 2,2,2-Trifluoro-N-(2-(3-nitrophenyl)ethyl)-N-phenylacetamide

This was prepared following a process analogous to that of Example 1, step (a).

(c) 2,2,2-Trifluoro-N-(2-(3-aminophenyl)ethyl)-N-phenylacetamide

This was prepared following a process analogous to that of Example 1, step (c).

(d) N-(3-(2-(Phenylamino)ethyl)phenyl)-2-thiophenecarboximidamide dihydrobromide This was prepared following a process analogous to that of Example 1, step (e). m.p. 235–240° C. (dec).

EXAMPLE 21

The following compounds were prepared following a process analogous to that of Example 17:

(a) N-(4-(2-(Ethylamino)ethyl)-phenyl)-2-thiophenecarboximidamide dihydrobromide, m.p. 176–178° C.

(b) N-(4-(2-(2-Propylamino)ethyl)phenyl)-2-thiophenecarboximidamide dihydrobromide, m.p. 240–242° C. (dec)

(c) N-(4-(2-(1-Propylamino)ethyl)phenyl)-2-thiophenecarboximidamide dihydrobromide, m.p. 233–235° C. (dec)

(d) N-(4-(2-(t-Butylamino)ethyl)phenyl)-2-thiophenecarboximidamide dihydrobromide, m.p. 241–242° C.

(e) N-(4-(2-(n-Butylamino)ethyl)phenyl)-2-thiophenecarboximidamide dihydrobromide, m.p. 238–240 ° C.

(f) N-(3-(2-(Methylamino)ethyl)phenyl)-2-thiophenecarboximidamide dihydrobromide, m.p. 219–223° C.

(g) N-(3-(2-(1-Propylamino)ethyl)phenyl)-2-thiophenecarboximidamide dihydrobromide, m.p. 72–75° C. (softened)

(h) N-(3-(2-(t-Butylamino)ethyl)phenyl)-2-thiophenecarboximidamide dihydrobromide, m.p. 232–235° C. (dec)

(i) N-(3-(2-(2-Propylamino)ethyl)phenyl)-2-thiophenecarboximidamide dihydrobromide, m.p. 206–210° C. (dec)

(j) N-(3-(2-aminoethyl)phenyl)-2-thiophenecarboximidamide dihydrobromide, m.p. 194–199° C.

(k) N-(3-(2-(Dimethylamino)ethyl)phenyl)-2-thiophenecarboximidamide dihydrobromide, m.p. 232–233° C. (dec)

(l) N-(3-(2-(Diethylamino)ethyl)phenyl)-2-thiophenecarboximidamide dihydrobromide. m.p. 75–80° C. (softened)

(m) N-(3-(2-(2-(1,2,3,4-Tetrahydro)isoquinolinyl)ethyl)phenyl)-2-thiophenecarboximidamide dioxalate. m.p. 172–175° C. (dec)

(n) N-(4-(3-(2-(1,2,3,4-tetrahydro)isoquinolyl)propyl)phenyl)-2-thiophene carboximidamide dioxalate, m.p. 138–142° C.

(o) N-(4-(2-(3,5-bistrifluoromethylphenylmethyl)amino)ethyl)phenyl-2-thiophenecarboximidamide free base, m.p. 98–100° C.

(p) N-(4-(2-(diethylamino)ethyl)phenyl-2-thiophenecarboximidamide free base m.p. 113–115° C.

(q) N-(4-(2-((3-chlorophenylmethyl)amino)ethyl)phenyl)-benzenecarboximidamide dihydrochloride, 253–254° C.

(r) N-(4-(2-((3-chlorophenylmethyl)amino)ethyl)phenyl)-3-chlorothiophene-2-carboximidamide dihydrochloride, 257° C.

(s) N-(4-(2-((4-methylphenylmethyl)amino)ethyl)phenyl)-2-thiophenecarboxamidine dihydrochloride, 218–219° C.

(t) N-(4-(2-(piperonylamino)ethyl)phenyl)-2-thiophenecarboxamidine dihydrochloride, m.p. 205–6° C.

EXAMPLE 22

The following compounds were prepared following a process analogous to that of Example 18:

(a) N-(3-(2-(((2-Chlorophenyl)methyl)amino)ethyl)phenyl)-2-thiophenecarboximidamide dioxalate, m.p. 155–157° C. (dec)

(b) N-(3-(3-((Phenylmethyl)amino)propyl)phenyl)-2-thiophenecarboximidamide dioxalate, m.p. 138–141° C. (dec)

(c) N-(4-(2-(((3-Chlorophenyl)methyl)amino)ethyl)phenyl)-2-thiophenecarboxamidine dioxalate, m.p. 216–217° C.

(d) N-(4-(2-(((4-Chlorophenyl)methyl)amino)ethyl)phenyl)-2-thiophenecarboxamidine dioxalate, m.p. 203–204° C.

(e) N-(4-(2-(((3-Chlorophenyl)methyl)amino)ethyl)phenyl)-3-chlorothiophene-2-carboximidamide dihydrochloride m.p. 257–258° C.

(f) N-(4-(3-(ethylamino)propyl)phenyl-2-thiophenecarboximidamide dioxalate, m.p. 98–100° C.

EXAMPLE 23

The following compound was prepared following a process analogous to that of Example 19:

(a) N-(3-(2-((N-Phenylmethyl-N-methyl)amino)ethyl)phenyl)-2-thiophenecarboximidamide, free-base m.p. 85–87° C.

(b) N-(4-(2-((N-Phenylmethyl-N-methyl)amino)ethyl)phenyl)-2-thiophene carboximidamide, free base m.p. 110–112° C.

(c) N-(3-(2-(((3-Chlorophenyl)methyl)amino)ethyl)phenyl)-2-thiophenecarboximidamide dioxalate, m.p. 185–88° C. (dec)

(d) N-(3-(2-(((3-fluorophenyl)methyl)amino)ethyl)phenyl)-2-thiophenecarboximidamide dioxalate, m.p. 183–4° C.

(e) N-(4-(3-(((3-Chlorophenyl)methyl)amino)propyl)phenyl)-2-thiophene carboximidamide dioxalate, m.p. 212–215° C.

(f) N-(4-(3-(((phenylmethyl-N-methyl)amino)propyl)phenyl)-2-thiophene carboximidamide dihydrobromide, m.p. 228–232° C. (dec)

(g) N-(4-(2-((ethyl)(phenylmethyl)amino)ethyl)phenyl)-2-thiophenecarboximidamide free base, m.p. 87–89° C.

(h) N-(4-(2-((propyl)(phenylmethyl)amino)ethyl)phenyl)-2-thiophenecarboximidamide free base m.p. 100–102° C.

(i) N-(4-(2-((1,1-dimethylethyl)(phenylmethyl)amino)ethyl)phenyl)-2-thiophenecarboximidamide free base, m.p. 145–148° C.

(j) N-(4-(2-(((3,4-dichlorophenyl)methyl)amino)ethyl)phenyl)-2-thiophenecarboximidamide free base, m.p. 111–114° C.

EXAMPLE 24

N-(4-3-((phenylamino)carbonyl)propyl)phenyl)-2-thiophenecarboximidamide (a) 4-(3-((phenylamino)carbonyl)propyl)aniline A stirred solution of 4-(4-nitrophenyl)butyric acid (5.0 g, 0.023 moles) in 20 ml of thionyl chloride was refluxed for 4 hours. The solvent was evaporated and the crude aid chloride, 2.5 g, was added dropwise to a stirred solution of aniline (2.0 g, 0.02 moles) in 30 ml of tetrahydrofuran and 10 ml of triethylamine and the reaction was then stirred 18 hours. The triethylamine hydrochloride was removed by filtration and 50 ml of ethyl acetate was added to the organic phase. The organic phase was washed with 1×100 ml of 1 N hydrochloric acid and the dried over magnesium sulfate. The solvent evaporated to yield a yellow solid. The solid was dissolved in 100 ml of methanol and 250 mg of 10% palladium on carbon was added, the reaction was hydrogenated over a 4 hour period. The product was found to be unreduced, and was then dissolved in 100 ml of methanol. 10 ml of a saturated solution of HCl in isopropanol was added, followed by 250 mg of 10% palladium on carbon. The mixture was hydrogenated for 4 hours. The catalyst was removed by filtration and the solvent evaporated. The residue was dissolved in 100 ml of hot water with a minimal amount of methanol, and the solution was then made basic with 50% sodium hydroxide solution. The mix was extracted with 150 ml of ethyl acetate, the extract was dried with magnesium sulphate and evaporated, giving solid 4-(3-(((phenyl)amino)carbonyl)propyl)aniline, yield 1.0 g, one spot on TLC.

(b) N-(4-(3-((phenylamino)carbonyl)propyl)phenyl)-2-thiophenecarboximidamide

To a stirred suspension of the product of step (a) (1.00 g; 0.0037 moles) in approximately 5 ml of isopropanol was added S-methyl-2-thiophenethiocarboximide hydroiodide (the product of Example 1, step (d)) (1.01 g, 0.0035 moles). The mixture was refluxed for 1 hr and then allowed to cool giving solids. The product was filtered and allowed to dry under vacuum overnight giving N-(4-(3-((phenylamino)carbonyl)propyl)phenyl)-2-thiophenecarboximidamide, 1.76 g yield. m.p. 229–231° C.

EXAMPLE 25

The following compounds was prepared following a process analogous to that of Example 24:

(a) N-(4-(3-((phenylmethylamino)carbonyl)propyl)phenyl)-2-thiophenecarboximidamide, m.p. 169–171° C.

(b) N-(4-(3-((1-pyrrolidyl)carbonyl)propyloxy)phenyl)-2-thiophenecarboximidamide, m.p. 191–194° C.

(c) N-(4-(3-((4-morpholinyl)carbonyl)propyloxy)phenyl)-2-thiophenecarboximidamide, m.p. 136–138° C.

(d) N-(4-(2-((phenylmethylamino)carbonyl)ethyl)phenyl)-2-thiophenecarboximidamide, m.p. 63–65° C.

(e) N-(3-(2-((phenylamino)carbonyl)ethyl)phenyl)-2-thiophenecarboximidamide, m.p. 203–205° C.

(f) N-(4-(3-((phenylamino)carbonyl)propyl)phenyl)-2-pyrrolecarboximidamide, m.p. 195–196° C.

(g) N-(4-(3-((phenylamino)carbonyl)propyl)phenyl)-2-furocarboximidamide, m.p. 197–199° C.

(h) N-(4-(3-((phenylamino)carbonyl)propyl)phenyl)-3-chloro-2-thiophenecarboximidamide, m.p. 141–144° C.

(i) N-((3-((phenylamino)carbonyl)propyl)phenyl)-1-methylpyrrole-2-carboximidamide, m.p. 154–155° C.

(j) N-(4-(3-(1-(4-methylpiperazinyl)carbonyl)propyl)phenyl)-2-thiophenecarboximidamide, m.p. 132–134° C.

EXAMPLE 26

N-(4-(3-((1-pyrrolidyl)carbonyl)propyl)phenyl)thiophene-2-carboximidamide hydroiodide (a) 4-(3-((1-pyrrolidinyl)carbonyl)propyl)aniline 4-(4-nitrophenyl)butyric acid (2.25 g, 0.01076 moles) was dissolved in 40 ml dichloromethane and cooled to −5° C. on an ice/acetone bath. Triethylamine (1.09 g, 0.01076 moles) and ethyl chloroformate (1.17 g, 0.01076 moles) were added and the mixture was stirred for 10 minutes before pyrrolidine (0.92 g, 0.01291 moles) was added dropwise whilst maintaining the temperature below 0° C. After 10 minutes the cold bath was removed and the reaction stirred for 16 hours at room temperature. The dichloromethane solution was washed with 2×75 ml saturated sodium bicarbonate and 2×75 ml water. The dichloromethane layer was dried over magnesium sulfate and the solvent evaporated under vacuum to leave 2.19 g of a clear brown oil. The clear brown oil was reduced under 50 psi hydrogen; ethanol was the solvent and 10% palladium on carbon was used as a catalyst. After 4 hours the catalyst was filtered off and the solvent evaporated under vacuum to provide 4-(3-((1-pyrrolidinyl)carbonyl)propyl)aniline, an oil that solidified on standing (this was used as is).

(b) N-(4-(3-((1-pyrrolidyl)carbonyl)propyl)phenyl)-2-thiophenecarboximidamide hydroiodide S-methyl-2-thiophenethiocarboximide hydroiodide (the product of Example 1, step (d)) (1.53 g 0.00538 moles) was added to the product step (a) (1.50 g 0.00646 moles), in 6 ml of isopropanol and stirred at room temperature for 16 hours. The resulting suspension of solids was diluted with 50 ml isopropanol and the solids collected by filtration to give N-(4-(3-((1-pyrrolidyl)carbonyl)propyl)phenyl)-2-thiophenecarboximidamide hydroiodide, mp 213–216° C.

EXAMPLE 27

The following compounds were prepared following a process analogous to of Example 26:

(a) N-(4-(3-((4-morpholinyl)carbonyl)propyl)phenyl)-2-thiophenecarboximidamide hydroiodide, m.p. 189–192° C.

(b) N-(4-((phenylamino)carbonyl)phenyl)-2-thiophenecarboximidamide, m.p. 200–201° C.

(c) N-(4-(2-((4-morpholinyl)carbonyl)ethyl)phenyl)-2-methylthiazole-4-carboximidamide, m.p. 280–281° C.

EXAMPLE 28

N-(4-(2-(((4-morpholinyl)carbonyl)amino)ethyl)phenyl)thiophene-2-carboximidamide hydroiodide (a) 4-(2-(((4-morpolinyl)carbonyl)amino)ethyl)aniline hydrochloride To a stirred solution of 4-nitrophenethylamine hydrochloride (4.0 g, 0.24 moles ) in 50 ml of tetrahydrofuran was added 10 ml of triethylamine. To this was added 4-morpholinecarbonyl chloride (3.6 g; 0.024 moles) dropwise in 20 ml of tetrahydrofuran and the reaction stirred for 6 hours. The triethylamine salt was removed by filtration, and the organic phase was washed with 1×100 ml of 1 N hydrochloric acid. The organic phase was dried over magnesium sulfate; evaporation of the solvent gave a crude oil. The crude oil was then dissolved in 250 ml of methanol, to this was added 250 mg of 10% palladium on carbon and the reaction hydrogenated for 4 hours. The catalyst was removed by filtration, and the solvent evaporated. To the residue was added 150 ml of ethyl acetate and hydrochloric acid gas was then added to make the salt. Upon cooling 4-(2-(((4-morpolinyl)carbonyl)amino)ethyl)aniline hydrochloride, a pink solid, crystallized and was collected by filtration, 4.4 g.

(b) 4-(2-(((4-morpolinyl)carbonyl)amino)ethyl)aniline

The product of step (a), 4.4 g, was dissolved in 200 ml of water. The mixture was made basic with 50% sodium hydroxide solution, and extracted with 2×50 l of ethyl acetate. The ethyl acetate extracts were combined, dried with magnesium sulfate, and evaporated in vacuo, giving a solid. The solid was dissolved in hot ethyl acetate and hexane, and crystals of 4-(2-(((4-morpolinyl)carbonyl)amino)ethyl)aniline formed on cooling. Analysis: calculated C 62.63 H 7.68 N 16.85; found C 62.43 H 7.65 N 16.59.

(c) N-(4-(2-(((4-morpolinyl)carbonyl)amino)ethyl)phenyl)-2-thiophenecarboximidamide hydroiodide The product of step (b), 1.0 g, and S-methyl-2-thiophenethiocarboximide hydroiodide (the product of Example 1, step (d)) 1.09 g, were combined in a minimal amount of isopropanol. The mixture was refluxed for one hour. The resulting solution was cooled, solids precipitated and were collected by fitration, giving N-(4-(2-(((4-morpolinyl)carbonyl)amino)ethyl)phenyl)-2-thiophenecarboximidamide hydroiodide, 0.95 g, m.p. 209–211° C.

EXAMPLE 29

N-(4-(3-(((phenyl)amino)carbonyl)propyloxy)phenyl)-2-thiophenecarboximidamide hydroiodide (a) 4-(4-nitrophenoxy)butyric acid Ethyl 4-bromobutyrate, 9.9 g, 4-nitrophenol, 7.0 g, and sodium carbonate, 6.0 g, were combined in 50 ml of DMF, and the mixture was warmed on a 100 C. hot plate for four hours. The solids were removed by filtration, and washed with 20 ml of acetone, the filtrate was diluted to 400 ml with cold water, and extracted with a combination of 50 ml ethyl acetate and 50 ml of hexanes. The resulting organic layer was washed with 3×200 ml of 0.2 M potassium carbonate to remove unreacted nitrophenol. The resulting organic layer was evaporated in vacuo to give 11 g of yellow oil. The crude yellow oil was diluted with 200 ml of methanol, treated with 25 ml of 2 M sodium hydroxide, and stirred over night at room temperature. The mixture was evaporated in vacuo, and diluted with water to 250 ml. The solution was clairified with celite, and then acidified with 20 ml of 4 M hydrochloric acid. The resulting solids were collected by filtration, washed with water, and dried in vacuo to give 4-(4-nitrophenoxy)butyric acid, mp 116–118° C.

(b) 4-(3-(((phenyl)amino)carbonyl)propyloxy)aniline

A solution of 4-(4-nitrophenoxy)butryic acid, 4.0 g, in 20 ml of thionyl chloride was refluxed for four hours, and then the excess thionyl chloride was evaporated in vacuo. The rude acid chloride was the added to a solution of aniline, 1.68 g, and triethylamine, 10 ml, in 30 ml of THF, and the reaction was stirred for 18 hours. The solids were removed by filtration, and the filtrate was diluted with 50 ml of ethyl acetate. The solution was washed with 100 ml of 1 N hydrochloric acid, dried with magnesium sulfate, and evaporated to give a solid. The solid was disolved in 100 ml of methanol, and hydrogenated with with 10% Pd/C for a total of 40 hours giving 1.25 g of 4-(3-(((phenyl)amino)carbonyl) propyloxy)aniline, a white solid. M.S. (M+H)$^+$=271.

(c) N-(4-(3-(((phenyl)amino)carbonyl)propyloxy)phenyl)-2-thiophenecarboximidamide hydroiodide The product of step (b), 1.0 g, and S-methyl-2-thiophenethiocarboximide hydroiodide (the product of Example 1, step (d)), 1.01 g, were combined in a minimal amount of isopropanol and the mixture refluxed for one hour. The resulting clear solution was cooled, solids precipitated and were collected by filtration, giving N-(4-(3-(((phenyl)amino)carbonyl)propyloxy)phenyl)-2-thiophenecarboximidamide hydroiodide, 1.76 g, m.p. 229–231° C.

EXAMPLE 30

N-(4-(2-(((trifluoromethyl)carbonyl)amino)ethyl) phenyl)-2-thiophenecarboximidamide (a) 4-(2-(((trifluoromethyl)carbonyl)amino)ethyl) nitrobenzene To a stirred solution of 4-nitrophenethylamine hydrochloride (1.84 g, 9.10 mmol) and triethylamine (3.03 ml, 21.70 mmol) in methanol (12 ml) was added trifluoroacetic anhydride (1.51 ml, 10.66 mmol) dropwise. After stirring for 1 minute, the solvent was removed at reduced pressure and the remaining residue was mixed with water and extracted with methylene chloride (3×20 ml). The combined extracts were washed with water, dried over magnesium sulfate, filtered, and concentrated to yield a solid which was recrystallized from methylene chloride/hexane to give 4-(2-(((trifluoromethyl)carbonyl)amino)ethyl)nitrobenzene as a white solid: 1.92 g (80% yield); m.p. 103–104° C.

(b) 4-(2-(((trifluoromethyl)carbonyl)amino)ethyl)aniline

To a stirred solution of the product of step (a) (0.52 g, 1.98 mmol) in THF/MeOH (100 ml, 1:1) was added a catalytic amount of 10% Pd/C. The mixture was hydrogenated at 50 psi for 1 hr, filtered through celite, and concentrated to give 4-(2-(((trifluoromethyl)carbonyl)amino)-ethyl)aniline which was homogeneous by TLC and used immediately in the next reaction.

(c) N-(4-(2-(((trifluoromethyl)carbonyl)amino)ethyl) phenyl)-2-thiophenecarboximidamide To a solution of the product of step (b) (0.30 g, 1.29 mmol) in isopropanol (6 ml) was added S-methyl-2-thiophenethiocarboximide hydroiodide (the product of Example 1, step (d)) (0.37 g, 1.29 mmol). The mixture was stirred for 4 hr, turned into a solution of saturated NaCl (50 ml) and 50% NaOH (4 ml), and extracted with ethyl acetate (3×20 ml). The combined extracts were washed with water, dried over magnesium sulfate, filtered and concentrated to a solid which was recrystallized from hexane/ethyl acetate to yield N-(4-(2-(((trifluoromethyl)carbonyl)amino)ethyl) phenyl)-2-thiophenecarboximidamide as a slightly yellow solid: 0.19 g (43% yield). m.p. 181–182° C.

EXAMPLE 31

N-(4-(2-(((methyl)carbonyl)amino)ethyl)phenyl)-2-thiophenecarboximidamide (a) 4-(2-(((methyl)carbonyl)amino)ethyl)nitrobenzene The above compound was made by the mothod of Example 30 step (a) except that trifluoroacetic anhydride was replaced by acetic anhydride, 1.28 g of a pale yellow solid was obtained that was used immediately in the next reaction.

(b) 4-(2-(((methyl)carbonyl)amino)ethyl)aniline

To a stirred solution of the product of step (a) (0.82 g, 3.94 mmol) in THF/MeOH (100 ml, 1:1) was added 4 ml of 1 N HCl and a catalytic amount of 10% Pd/C. The mixture was hydrogenated at 50 psi for 4 hr, filtered through celite, and concentrated to give a solid. The solid was turned into a solution of saturated NaCl (50 ml) and 50% NaOH (4 ml), and extracted with ethyl acetate (3×20 ml). The combined extracts were washed with water, dried over magnesium sulfate, filtered and concentrated to a solid which was used immediately in the next reaction.

(c) N-(4-(2-(((methyl)carbonyl)amino)ethyl)phenyl)-2-thiophenecarboximidamide

The above compound was prepared following the procedure of Example 30, step (c). After recrystallization from ethyl acetate/methanol, 0.56 g of a tan solid was obtained. mp. 186–187° C.

EXAMPLE 32

N-(4-(2-(((phenylmethyl)carbonyl)amino)ethyl) phenyl)-2-thiophenecarboximidamide (a) 4-(2-(((phenylmethyl)carbonyl)amino)ethyl) nitrobenzene The above compound was prepared following the procedure of Example 30, step (a) except that trifluoroacetic anhydride was replaced by phenylacetyl chloride. 1.42 g of a pale yellow solid was obtained that was used immediately in the next reaction.

(b) 4-(2-(((phenylmethyl)carbonyl)amino)ethyl)aniline

The above compound was prepared by an analogous process to that described in Example 8. step (b). The oil obtained was used immediately in the next reaction.

(c) N-(4-(2-(((phenylmethyl)carbonyl)amino)ethyl)phenyl)-2-thiophenecarboximidamide The above compound was prepared following the procedure of Example 30, step (c). After recrystallization from ethyl acetate/methanol, 0.45 g of a tan solid was obtained. mp. 210–211° C.

EXAMPLE 33

N-(4-(2-(((phenyl)carbonyl)amino)ethyl)phenyl)-2-thiophenecarboximidamide (a) 4-(2-(((phenyl)carbonyl)amino)ethyl)nitrobenzene The above compound was prepared following the procedure of Example 30, step (a) except that trifluoroacetic anhydride was replaced by benzoyl chloride. 1.77 g of a pale yellow solid was obtained that was used immediately in the next reaction.

(b) 4-(2-(((phenyl)carbonyl)amino)ethyl)aniline

The above compound was prepared by an analogous process to that described in Example 8, step (b). The oil obtained was used immediately in the next reaction.

(c) N-(4-(2-((phenyl)carbonyl)amino)ethyl)phenyl)-2-thiophenecarboximidamide

The above compound was prepared following the procedure of Example 30, step (c). After recrystallization from ethyl acetate/methanol, 1.10 g of a tan solid was obtained. m.p. 196–197° C.

EXAMPLE 34

N-(4-(((phenyl)iminocarbonyl)amino)phenyl)-2-thiophenecarboximidamide (a) N-(4-nitrophenyl)benzenecarboximidamide To a stirred solution of benzonitrile (25 ml) was added a catalytic amount of 4-dimethylaminopyridine. To this was added 4-nitroaniline hydrobromide (10.0 g, 0.57 moles) and the reaction then heated to 190° C. for six hours. The reaction mixture was allowed to cool and 25 ml isopropanol was added. A solid was collected by filtration to yield 8.6 g of N-(4-nitrophenyl)benzenecarboximidamide, m.p. 240–241° C.

N-(4-aminophenyl)benzenecarboximidamide

To a pressure bottle charged with the product of step (a) (8.6 g, 0.024 moles) in 200 ml of methanol was added 20 ml of isopropanol/HCl and 0.5 g of 10% palladium on carbon. The reaction was hydrogenated for six hours; the catalyst was removed by filtration and the solvent evaporated. To the residue was added 50 ml of isopropanol and 100 ml of ethyl acetate, the solid was slurried and then collected by filtration to yield 10.6 g of N-(4-aminophenyl)benzenecarboximidamide hydrochloride. The N-(4-aminophenyl)benzenecarboximidamide hydrochloride was dissolved in 100 ml of water and 20 ml of 50% sodium hydroxide. The aqueous phase was extracted (3×100 ml) of ethyl acetate, and dried over magnesium sulfate. Evaporation of the solvent gave solid product N-(4-aminophenyl) benzene carboximidamide, yield 7.6 g.

(c) N-(4-(((phenyl)iminocarbonyl)amino)phenyl)-2-thiophenecarboximidamide

To a stirred suspension of the product of step (b) (1.1 g, 0.0052 moles) in 5 ml of isopropanol was added S-methyl-2-thiophenecarboxthioimide hydroiodide (the product of Example 1, step (d)) (1.5 g, 0.0054 moles) and the reaction was stirred for 48 hours. The solid was collected by filtration, this was dissolved in a solution containing 100 ml of water and 10 ml of 50% sodium hydroxide and the aqueous phase was extracted three times with ethyl acetate (100 ml). The organic phase was dried over magnesium sulfate and subsequent evaporation of the solvent gave a crude oil. The crude oil was dissolved in 20 ml of methanol of HCl gas was added upon standing a solid crystallized and was collected by filtration. The product N-(4-(((phenyl)iminocarbonyl)amino)phenyl)-2-thiophenecarboximidamide was dried at 80° C. for 24 hrs. m.p. 317–318° C.

EXAMPLE 35

The following compounds were prepared following a method analogous to that of Example 34:
(a) N-N"-(1,4-phenylene)bis-2-thiophenecarboximidamide hydroiodide, m.p. 278–279° C.
(b) N-N"-(1,3-phenylene)bis-2-thiophenecarboximidamide, m.p. 219–220° C.
(c) N,N'-(1,3-phenylene)bis-2-chlorophenylcarboximidamide dimaleate, m.p. 200–201° C.
(d) N,N'-(1,4-phenylene)bis-3-chlorothiophene-2-carboximidamide free base, m.p. 247–248° C.
(e) N-(4-(((2-methoxyphenyl)iminocarbonyl)amino)phenyl)-2-thiophene carboximidamide free base, m.p. 187–188° C.
(f) N-(4-(((Phenyl)iminocarbonyl)amino)phenyl)-3-chlorothiophene-2-carboximidamide free base, m.p. 213–214° C.
(g) N-(4-(((Phenyl)iminocarbonyl)amino)phenyl)-3-thiophene carboximidamide dihydrochloride, m.p. 323–324° C.
(h) N-(3-(((phenyl)iminocarbonyl)amino)phenyl)-2-thiophenecarboximidamide m.p. 295–296° C.
(i) N-(4-(((4-chlorophenyl)iminocarbonyl)amino)phenyl)-2-thiophenecarboximidamine dihydrochloride, m.p. 296–297° C.
(j) N-(4-(((2-chlorophenyl)iminocarbonyl)amino)phenyl)-2-thiophenecarboximidamide dioxalate, m.p. 166–167° C.
(k) N-(4-(((4-bromophenyl)iminocarbonyl)amino)phenyl)-2-thiophenecarboximidamide dioxalate, m.p. 236–237° C.
(l) N-(4-(((3-chloro-4-methylphenyl)iminocarbonyl)amino)phenyl)-2-thiophenecarboximidamide dihydrochloride, m.p. 294–294° C.
(m) N-(4-(((3,5-dimethoxyphenyl)iminocarbonyl)amino)phenyl)-2-thiophenecarboximidamide dioxalate, m.p. 226–227° C.
(n) N-(4-(((3,5-dichlorophenyl)iminocarbonyl)amino)phenyl)-2-thiophenecarboximidamide dioxalate, m.p. 237–238° C.
(o) N-(4-(((Phenyl)iminocarbonyl)amino)phenyl)-2-furancarboximidamide dioxalate m.p. 210–211° C.
(p) N-(4-(((3-methylphenyl)iminocarbonyl)amino)phenyl)-2-thiophenecarboximidamide free base m.p. 205–206° C.
(q) N-(4-(((3-Methoxyphenyl)iminocarbonyl)amino)phenyl)-2-thiophenecarboximidamide free base m.p. 194–195° C.
(r) N-(4-(((3-Bromophenyl)iminocarbonyl)amino)phenyl)-2-thiophenecarboximidamide dihydrobromide m.p. 293–294° C.
(s) N-(4-(((3-chlorophenyl)iminocarbonyl)amino)phenyl)-2-thiophenecarboximidamide dihydrochloride m.p. 310–311° C.
(t) N-(4-(((3-methylphenyl)iminocarbonyl)amino)phenyl)-2-pyrrolecarboximidamide dihydrobromide m.p. 210–211° C.
(u) N-(4-(((4-chlorophenyl)iminocarbonyl)amino)phenyl)-2-pyrrolecarboximidamide difumarate m.p. 228–229° C.

EXAMPLE 36

N-(4-(2-(((Phenylamino)carbonyl)amino)ethyl)phenyl)-2-thiophenecarboxamidine hydroiodide (a) N-(2-(4-Nitrophenyl)ethyl)N'phenyl urea Prior to running the reaction, a 3.09 g sample of 4-nitrophenylamine hydrochloride was dissolved in 20 mls water and treated with 30 mls 2N NaOH. The freebase was extracted with 2×75 mls diethyl ether. The ether layer was dried over magnesium sulfate, and the volume of the ether was reduced under vacuum to ~60 mls. To this solution was added 1.81 g of phenyl isocyanate dropwise. The white solids that precipitated upon addition were stirred for three hours, then were collected by filtration and washed with ether. Air drying left 3.67 g, N-(2-(4-Nitrophenyl)ethyl) N'phenyl urea, m.p. 170–172° C.
(b) N-(2-(4-aminophenyl)ethyl)N'phenyl urea To a pressure bottle charged with 3.67 g N-(2-(4-Nitrophenyl)ethyl)N'phenyl urea in 100 mls of a 50/50 volume mix of methanol/THF was added a catalyst amount of 5% Pd/C. The mix was hydrogenated under 50 psi hydrogen gas for 24 hours, the catalyst was filtered and TLC showed starting material and two lower Rf spots. The solvents were removed by evaporation in a vacuum and the resultant solid was taken up in methanol, and an excess of oxalic acid was added. The solution was quenched with ether and the precipitated white solids were collected by filtration. The solids were treated with 100 mls 2N NaOH, and the freebase was extracted with ethyl acetate; the organic layer was dried with magnesium sulfate and evaporated to leave a yellow solid; N-(2-(4-aminophenyl)ethyl) N'phenyl urea (430 mg).

(c) N-(4-(2-(((Phenylamino)carbonyl)amino)ethyl)phenyl)-2-thiophenecarboxamidine hydroiodide.

To a solution of 430 mg N-(2-(4-Nitrophenyl)ethyl) N'phenyl urea slurried in 3 mls of isopropyl alcohol was added 435 mg of S-methyl-2-thiophenecarboxamide dihydroiodide (the product of Example 1, step (d)). The mix was stirred for 16 hrs at room temperature. The suspension was diluted in 25 mls isopropyl alcohol and the solids were collected by filtration to leave a yellow/tan solid. The solids were recrystallized from methanol/ether. Two batches were collected and combined to give 470 mg of N-(4-(2-(((Phenylamino)carbonyl)amino)ethyl)phenyl)-2-thiophenecarboxamidine hydroiodide, m.p. 216–219° C.

EXAMPLE 37

The following compound was made by a process analogous to that of Example 37: N-(4-(2-(((phenylamino)carbonyl)oxy)ethyl)phenyl)-2-thiophenecarboximidamide, m.p. 222–224° C.

EXAMPLE 38

N-(4-((bis(phenylmethyl)amino)methyl)phenyl)-2-thiophenecarboximidamide (a) 4-((bis(phenylmethyl)amino)methyl)nitrobenzene To 4-nitrobenylamine (1.61 g, 10.60 mmol) in DMF (25 ml) was added potassium carbonate (3.22 g, 23.30 mmol) followed by benzyl bromide (2.64 ml, 22.30 mmol). The mixture was allowed to stir for 2 days, dumped into water and extracted with ethyl acetate(3×50 ml). The combined extracts were washed with water, dried over magnesium sulfate, filtered, concentrated and chromatographed over silica gel (20% ethyl acetate/hexane) to yield 4-((bis(phenylmethyl)amino)methyl) nitrobenzene: (1.64 g, 47%); M.S. (M+H)$^{30}$=333.

(b) 4-((bis(phenylmethyl)amino)methyl)aniline

To the product of step (a) (0.56 g, 1.69 mmol) in AcOH (15 ml) was added Tin(II) chloride dihydrate (2.00 g, 19.03 mmol) followed by concentrated HCl (5 ml). The mixture was stirred for 20 hr, cooled to 0° C., quenched with 50% NaOH, and extracted with ethyl acetate (3×50 ml). The combined extracts were washed with water, dried over magnesium sulfate, filtered, concentrated and chromatographed over silica gel (30% ethyl acetate/hexane) to yield 4-((bis(phenylmethyl)amino)methyl)aniline: (0.29 g, 57%); M.S. (M+H)$^+$=303.

(c) N-(4-((bis(phenylmethyl)amino)methyl)phenyl)-2-thiophenecarboximidamide

To a solution of the product of step (b) (0.28 g, 0.93 mmol) in isopropanol (6 ml) was added S-methyl-2-thiophenethiocarboximide hydroiodide (the product of Example 1, step (d)) (0.26 g, 0.93 mmol). The mixture was stirred for 14 hr, quenched with 2 N NaOH (2 ml) and extracted with ethyl acetate (3×30 ml). The combined extracts were washed with water, dried over magnesium sulfate, filtered, and concentrated to a solid which was recrystallized from ethyl acetate/hexane to yield N-(4-((bis(phenylmethyl)amino)methyl)phenyl)-2-thiophenecarboximidamide as a white solid: (86 mg, 22%); m.p. 127–128° C.

EXAMPLE 39

The following compound was prepared following a process analogous to that of Example 8:

N-(4-(2-aminomethyl)phenyl)-2-thiophenecarboximidamide hydrobromide, m.p. 188–189° C.

EXAMPLE 40

N-(3-(1,2,3,4-tetrahydroisoquinolin-2-ylmethyl) phenyl)-2-thiophenecarboximidamide dihydrobromide (a) 3-(1,2,3,4-tetrahydroisoquinolin-2-ylmethyl) nitrobenzene To 3-nitrobenzyl chloride (2.00 g, 11.66 mmol) in DMF (25 ml) was added potassium carbonate (1.93 g, 13.96 mmol) followed by tetrahydroisoquinoline (1.55 g, 11.66 mmol). The mixture was allowed to stir for 4 hr, dumped into water and extracted with ethyl acetate (3×50 ml). The combined extracts were washed with water, dried over magnesium sulfate, filtered, and concentrated to an oil. The oil was dissolved in ether and treated with IPA/HCl to afford 3-(1,2,3,4-tetrahydroisoquinolin-2-ylmethyl)nitrobenzene hydrochloride: (1.96 g, 55%); m.p. 196–197° C.

(b) 3-(1,2,3,4-tetrahydroisoquinolin-2-ylmethyl)aniline hydrochloride

To a stirred solution of the product of step (a) (1.00 g, 3.29 mmol) in THF/MeOH (100 ml, 1:1) was added a catalytic amount of 10% Pd/C. The mixture was hydrogenated at 50 psi for 0.5 hr, filtered through celite, and concentrated to give (3-(1,2,3,4-tetrahydroisoquinolin-2-ylmethyl)aniline hydrochloride which was homogeneous by TLC and used immediately in the next reaction.

(c) N-(3-(1,2,3,4-tetrahydroisoquinolin-2-ylmethyl)phenyl)-2-thiophenecarboximidamide To a solution of the product of step (b) (0.90 g, 3.29 mmol) in isopropanol (3 ml)/DMF (1 ml) was added S-methyl-2-thiophenethiocarboximide hydroiodide (the product of Example 1, step (d)) (0.94 g, 3.29 mmol). The mixture was stirred for 14 hr, quenched with 2 N NaOH (2 ml) and extracted with ethyl acetate (3×30 ml). The combined extracts were washed with water, dried over magnesium sulfate, filtered, and chromatographed over silica gel (8% methanol/methylene chloride) to yield the title compound as the free base. Treatment with IPA/HBr yielded N-(3-(1,2,3,4-tetrahydroisoquinolin-2-ylmethyl)phenyl)-2-thiophenecarboximidamide as a white solid: (0.26 g, 16%); m.p. dec>179° C.

EXAMPLE 41

N-(4-(4-((phenylmethyl)amino)butyl)phenyl)-2-thiophenecarboximidamide dimaleate (a) 4-(4-nitrophenyl)-N-(phenylmethyl)butylamide A sample of 4-(4-nitrophenyl)butyric acid, 2.09 g, dissolved in 20 ml of dichloromethane was treated with benzylamine, 1.07 g, giving suspended solids. The mix was treated with diphenylphosphorylazide, 2.75 g, and 20 ml of dioxane and on stirring for 4 hours it became clear. The mix was diluted with 100 ml of ethyl acetate and washed twice with 100 ml of 2 M potassium carbonate, then 100 ml of 1 M hydrochloric acid. The organic layer was dried with magnesium sulfate and evaporated to give solids. The solids were dissolved in 150 ml of cyclohexane and 50 ml of ethyl acetate, and cooled to give white solids; these solids were collected by filtration and air dried to give 4-(4-nitrophenyl)-N-(phenylmethyl)butylamide mp 133–135° C.

(b) 4-(4-aminophenyl)-N-(phenylmethyl)butylamide hydrochloride

A sample of the product of step (a), 0.80 g in 20 ml of ethanol and 20 ml of ethyl acetate was treated with 0.4 g of 5% paladium on carbon and placed under 50 psi of hydrogen. TLC after one hour showed a new spot, Rf 0.2 with 15% acetone in methylenechloride. The mix was evaporated to dryness, and then treated with 30 ml of toluene. The residue was dissolved in 10 ml of THF and treated with 5 ml of 1 M lithium aluminium hydride in THF (Aldrich) giving a clear solution. After one hour at room temperature, 1 ml of 2M sodium hydroxide was added dropwise, followed by 10 g of anhydrous sodium sulfate. After stirring for 30 minutes, the mix was filtered and treated with hydrogen chloride gas and an oil formed. The mix was treated with 3 ml of isopropanol, and further hydrogen chloride gas, giving solids. The mix was cooled to –20° C. for 2 hours, then filtered and air dried to give 4-(4-aminophenyl)-N-(phenylmethyl) butylamide hydrochloride; Chloride analysis: calc 20.78 found 20.64

(c) 4-(4-((phenylmethyl)amino)butyl)aniline dihydrochloride

A sample of the produce of step (b) was suspended in 5 ml of THF and treated with 5 ml of 1M lithium aluminium hydride in THF (Aldrich) giving a clear solution. The mixture was warmed to reflux for 5 hours, then cooled. The semisolid mass was diluted with diethyl ether to 20 ml, and then 1 ml of 2M sodium hydroxide was added dropwise, followed by 4 cm³ of anhydrous sodium sulfate. After stirring for 15 minutes, the mix was filtered and the solids were washed with 20 ml of diethyl ether. The combined filtrates were treated with hydrogen chloride gas and allowed to stand at room temperature. The solids that formed were collected by filtration and dried in vacuo to give 4-(4-(phenylmethyl)amino)butyl)aniline dihydrochloride; Chloride analysis: calc 21.66 found 21.63

(d) N-(4-(4-((phenylmethyl)amino)butyl)phenyl)-2-thiophenecarboximidamide dimaleate A sample of the produce of step (c), 0.50 g, and S-methyl-2-thiophenethiocarboximide hydroiodide (the product of Example 1, step (d)), 0.44 g were combined in 4 ml of isopropanol and warmed to 60° C. After 2 hours, TLC with 15% methanol in chloroform on silica showed that the starting aniline was mostly consumed, and that there had developed a new spot of lower Rf. The mix was diluted with 20 ml of 1M potassium carbonate, and extracted with ethyl acetate. The ethyl acetate extract was dried with 10 g of potassium carbonated and treated with 0.150 g of maleic acid, giving a gummy precipitate. TLC of the precipitate versus the supernatant showed the precipitate to be a mix of the starting amine and product, and the supernatant contained mostly product. The supernatant was then treated again with 0.150 g of maleic acid, giving a gummy precipitate, and the remaining supernatant was decanted. The solids were dissolved in 5 ml of methanol and precipitated with 100 ml of diethylether. The resulting gummy precipitate was reacted with 1 ml of water, diluted with acetone to 200 ml giving a clear solution, diluted with diethyl ether to 275 ml and cooled to –20° C. The solids were collected by filtration, washed with 20 ml of diethyl ether, and dried in vacuo to provide N-(4-(4-((phenylmethyl) amino)butyl)phenyl)-2-thiophenecarboximidamide dimaleate, m.p. 104–106° C.

EXAMPLE 42

N-(4-((((2-thiophenyl)iminomethyl)amino)methyl) phenyl)-2-thiophenecarboximidamide difumarate (a) 4-aminomethylaniline To a solution of 4-nitrobenzylamine hydrochloride (9.0 g, 0.0477) in methanol (200 ml) was added 20 ml of IPA/HCl and a catalytic amount of 10% palladium on carbon. The mixture was hydrogenated at 50 psi for 4 hrs, filtered through celite, concentrated to a solid. The above solid was then dissolved in 300 ml of water and 20 ml of 2N sodium hydroxide and extracted into methylene chloride (3×100 ml). The combined extracts were dried over magnesium sulfate, filtered and concentrated to give 4-aminomethylaniline as an oil (6.1 g).

(b) N-(4-((((2-thiophenyl)iminomethyl)amino)methyl) phenyl)-2-thiophenecarboximidamide difumarate To a stirred solution of 4-aminomethylaniline (1.6 g, 0.0013 mmol) in (10 ml) dimethylformamide and (10 ml) of isopropanol was added S-methyl-2-thiophenethiocarboximide hydroiodide (the product of Example 1, step (d)) (4.4 g, 0.015 mmol). The mixture the heated to 40° C. for 72 hrs. The reaction was diluted with 20% aqueous sodium hydroxide, and the solids collected by filtration to yield (2.5 g). The fumaric acid salt was made from isopropanol and methanol, to yield (2.0 g) of N-(4-(((2-thiophenyl)iminomethyl)amino)methyl)phenyl)-2-thiophenecarboximidamide difumarate, m.p. 200–201° C.

EXAMPLE 43

The following compounds were prepared by a process analogous to that to Example 17:

(a) N-(3-(3-(1-pyrrolidinyl)propyl)phenyl)-phenylcarboximidamide dioxalate, m.p. 138–139° C.

(b) N-(4-(2-((4-methoxyphenylmethyl)amino)ethyl) phenyl)-2-thiophenecarboximidamide free base, m.p. 144–145° C.

(c) N-(4-(2-((4-methylphenylmethyl)amino)ethyl) phenyl)-2-thiophenecarboximidamide monohydrochloride, m.p. 225–226° C.

(d) N-(3-(2-((3-phenylpropyl)amino)ethyl)phenyl)-2-thiophenecarboximidamide dihydrobromide m.p. 183–186° C.

(e) N-(3-(2-((2-methylphenylmethyl)amino)ethyl) phenyl)-2-thiophenecarboximidamide free base m.p. 114–116° C.

(f) N-[4-(2-((1-indanyl)ethyl)amino)phenyl]-2-thiophenecarboximidamide dioxalate, m.p. 95° C. (dec)

(g) N-(4-(2-(((4-pyridyl)methyl)amino)ethyl)phenyl)-2-thiophenecarboximidamide trihydrochloride m.p. >250° C.

(h) N-(4-(2-(((2-thienyl)methyl)amino)ethyl)phenyl)-2-thiophenecarboximidamide dioxalate m.p. 226–227° C.

EXAMPLE 44

N-(3-(2-((2-phenylethyl)amino)ethyl)phenyl)-2-thiophenecarboximidamide dihydrobromide (a) N-(2-phenylethyl)-3-nitrophenylacetamide 2.50 g (0.0138 moles) of 3-nitrophenylacetic acid were refluxed in 25 mls of thionyl chloride. The solvents were evaporated and the residue taken up in 50 mls of THF before 3.51 g (0.290 moles) of phenethylamine were added dropwise at 0° C. The mix was stirred for 48 hours and the hydrochloride salt of the amine was filtered off as a white solid. The wash was evaporated to leave N-(2-phenylethyl)-3-nitrophenylacetamide, a dull orange oil, 4.48 g. The product was analyzed by MS and NMR.

(b) N-(2-phenylethyl)-2-(3-nitrophenyl)ethylamine

To a stirred solution of the product of step (a), 4.48 g, (0.0158 moles) in 80 ml dry THF was added 47.4 ml of 1M Borane/THF. The mix was heated to reflux for 3 hours and cooled before 10 ml of methanol was added carefully followed by 20 ml of 4N HCl. The solution was concentrated by evaporation under vacuum to leave a reddish liquid. The oil was basified with 2M NaOH and the product extracted with 3×50 ml of EtOAc. The organic layers were combined, dried over magnesium sulfate and evaporated to leave an oil. The oil was dissolved in HCl/isopropanol solution. White solids formed and were collected by filtration to give N-(2-phenylethyl)-2-(3-nitrophenyl)ethylamine, 2.63 g, m.p. 196–200° C.

(c) N-(2-phenylethyl)-N-(2-(3-nitrophenyl)ethyl)trifluoroacetamide

To a slurry of the product of step (b), 2.63 g, (0.00857 moles) in 40 ml dichloromethane was added 1.99 g (0.0197 moles) of triethylamine and the mix was cooled to 0° C. before 2.34 g (0.111 moles) of trifluoroacetic anhydride was added dropwise. After 45 minutes, the mixture was quenched with 50 ml water and the product extracted with 3×50 ml dichloromethane. The organic layers were combined, dried over magnesium sulfate and evaporated to leave N-(2-phenylethyl)-N-(2-(3-nitrophenyl)ethyl)trifluoroacetamide, 3.3 g, as an oil.

(d) N-(2-phenylethyl)-N-(2-(3-aminophenyl)ethyl)trifluoroacetamide

To a solution of the product of step (c), 3.3 g, in 75 ml each of THF and methanol was added a catalytic amount of 10% Pd on carbon. After 1 hour under 50 psi hydrogen, the reaction was complete. The catalyst was filtered off and the solvents evaporated to leave N-(2-phenylethyl)-N-(2-(3-aminophenyl)ethyl) trifluoroacetamide, 2.88 g, as an oil.

(e) N-(3-(2-((2-phenylethyl)amino)ethyl)phenyl)-2-thiophenecarboximidamide dihydrobromide To a solution of the product of step (d), 2.88 g (0.00857 moles) in 15 ml isopropanol was added 2.94 g of S-methyl-2-thiophenethiocarboximide hydroiodide (the product of Example 1, step (d)). The mixture was stirred at room temperature for 16 hours then a solid yellow residue was filtered off and discarded. The wash was evaporated and the residue dissolved in minimal methanol; the solution was basified with 2M NaOH and heated to 50° C. for 30 minutes. The deprotected product was extracted with 3×50 ml ethyl acetate, the organic layers were combined, washed with 2×50 ml water, dried over magnesium sulfate and evaporated to leave an oil. The free base was dissovled in an isopropanol solution of HBr. Solids formed with the addition of ethyl acetate and cooling were collected by filtration to give 102 mg of N-(3-(2-((2-phenylethyl)amino)ethyl)phenyl)-2-thiophenecarboximidamide dihydrobromide salt. m.p. 137–139° C.

EXAMPLE 45

The following compounds were prepared by following a method analogous to that of Example 44:

(a) N-(4-(2-aminoethyl)phenyl)-2-pyrrolecarboximidamide dioxalate m.p. 145° C. (dec)

(b) (S)-N-(4-(2-((1-phenylethyl)amino)ethyl)phenyl)-2-thiophenecarboximidamide dihydrochloride m.p. 197° C. dec (c) (R)-N-(4-(2-((1-phenylethyl)amino)ethyl)phenyl)-2-thiophenecarboximidamide free base, m.p. 92–94° C.

(d) N-(3-(2-((4-phenylbutyl)amino)ethyl)phenyl)-2-thiophenecarboximidamide dihydrobromide, m.p. 136–139° C.

EXAMPLE 46

N-(4-(((phenylmethoxy)carbonyl)aminomethyl)phenyl)-2-thiophenecarboximidamide oxalate (a) 4-(((phenylmethoxy)carbonyl)aminomethyl)nitrobenzene A sample of 4-nitrobenzylamine hydrochloride, 5 g, and 200 ml of water was treated with sodium bicarbonate, 10 g. The mixture was treated with 50 ml of ethyl acetate, and then benzyl chloroformate, 4 ml. After 4 hours, the mix was treated with 200 ml of hexanes, and the precipitated solids were collected by filtration. The crude product was dissolved in 150 ml of hot methanol, filtered, diluted with 250 ml of water, and cooled. The resulting solids were collected to give 4-(((phenylmethoxy)carbonyl)aminomethyl)nitrobenzene, m.p. 92–93° C.

(b) 4-(((phenylmethoxy)carbonyl)aminomethyl)aniline

The product of step (a), 6.0 g was treated with 10 ml of acetic acid and 100 ml of methanol. The mixture was treated with platinum sulfide on carbon, 0.97 g, and treated with 50 psi of hydrogen gas; after 20 hours, the mixture was filtered and evaporated in vacuo. The residue was dissolved in 50 ml of ether, and diluted with hexanes to 200 ml. The mixture was then stirred for five days and filtered to give 4-(((phenylmethoxy)carbonyl)aminomethyl)aniline, m.p. 60–64° C.

(c) N-(4-(((phenylmethoxy)carbonyl)aminomethyl)phenyl)-2-thiophenecarboximidamide oxalate The product of step (b), 0.89 g, and S-methyl-2-thiophenethiocarboximide hydroiodide (the product of Example 1, step (d)), 1.0 g, were combined in 6 ml of isopropanol, and stirred at 30° C. After 4 hours, the mixture was precipitated with ether, giving gummy solids which were taken up in 100 ml of hot water, treated with cellite and filtered. The mix was cooled, giving gummy white solids which were treated with 50 ml of ethyl acetate and 5 g sodium bicarbonate. The ethyl acetate layer was dried with magnesium sulfate, and cooled to −20° C. The mix was then treated with hexanes, and failed to give crystals. The mix was evaporated in vacuo, and the crude free base, 0.7 g, was dissolved in 40 ml of warm isopropanol and treated with oxalic acid dihydrate, 0.26 g. On cooling and treatment with 150 ml of ether a tacky precipitate resulted. After stirring overnight at room temperature, the resulting solids were collected by filtration to yield N-(4-(((phenylmethoxy)carbonyl)aminomethyl)phenyl)-2-thiophene carboximidamide oxalate, m.p. 150–160° C.

EXAMPLE 47

N-(4-(2-((phenylmethyl)amino)ethoxy)phenyl)-2-thiophenecarboximidamide hydroiodide (a) 4-nitrophenoxy-N-(phenylmethyl)acetamide A sample of 4-nitrophenoxy-N-(phenylmethyl)acetic acid hydrazide (Lancaster), 4.22 g, was treated with 20 ml of 1M aqueous HCl and 200 ml of ethyl acetate. The mix was cooled to 10° C., and then 1.38 g of sodium nitrite in 20 ml of water was added over 2 minutes. The mix was stirred for 5 minutes, the layers were separated, and the ethyl acetate layer was dried with sodium sulfate. The ethyl acetate solution was treated with 5 ml of benzylamine, giving a prompt precipitate formation. After 20 minutes the mix was washed with 100 ml of saturated sodium carbonated, then 100 ml of 1M HCl (aqueous). The ethyl acetate layer was then evaporated. The solids were dissovled in 50 ml of acetone, and precipitated with water. The solids were collected by filtration to provide 4-nitrophenoxy-N-(phenylmethyl)acetamide, m.p. 125–126° C., 3.76 g.

(b) 4-aminophenoxy-N-(phenylmethyl)acetamide

A sample of the product of step (a), 3.74 g, was taken up in 100 ml of methanol and 100 ml of ethyl acetate. The mix was treated with 0.4 g of 10% palladium on carbon and placed under 50 psi hydrogen. After one hour the mix was filtered, and concentrated in vacuo to provide crude 4-aminophenoxy-N-(phenylmethyl) acetamide; CHN calculated: C 70.29, H 6.29 N 10.93, found C 69.97, H 6.3 N 10.90

(c) 4-(2-((phenylmethyl)amino)ethoxy)aniline

A solution of 3.2 g of the product of step (b) in 40 ml of dry THF under $N_2$ was treated with 40 ml of 1M diborane in THF. The mix was warmed to reflux for three hours, treated with 40 ml of 6M aqueous HCl, and refluxed for 2 hours. The filtrate was concentrated under vacuo to 150 ml. The cloudy mix was treated with 100 ml of crushed ice and neutralised with 50% NaOH. And the resulting fine solids were collected, washed with water, and dried by infrared to give 4-(2-((phenylmethyl)amino)ethoxy)aniline, MS=243, 98% by capillary electrophoresis (d) N-(4-(2-((phenylmethyl)amino)ethoxy)phenyl)-2-thiophenecarboximidamide hydroiodide A sample of 4-(2-((phenylmethyl)amino)ethoxy)aniline, 0.81 g and S-methyl-2-thiophenethiocarboximide hydroiodide (the product of Example 1, step (d)), 1.42 g were combined in 10 ml of isopropanol and stirred for 7 hours at room temperature. The resulting white solids were collected by filtration, washed with 10 ml of isopropanol, and dried in vacuo to provide white solids, N-(4-(2-((phenylmethyl)amino)ethoxy)phenyl)-2-thiophenecarboximidamide hydroiodide, m.p. 193–195° C.

EXAMPLE 48

N-[4-(((Diphenylamino)carbonyl)amino)phenyl]-2-thiophenecarboxamidine hydrochloride (a) 4-[Diphenylamino(carbonyl)amino]aniline To a stirred solution of 1,4-phenylenediamine (1.00 g, 9.25 mmol) and triethylamine (1.29 ml, 9.25 mmol) in methylene chloride (50 ml) was added diphenylcarbamyl chloride (2.14 g, 9.25 mmol). After stirring for 14 hr, the mixture was dumped into water and extracted with methylene chloride (3×20 ml). The combined extracts were washed with water, dried over magnesium sulfate, filtered, concentrated and chromatographed over silica gel (80% ethyl acetate/hexane) to yield 4-[diphenylamino(carbonyl)amino] aniline: (0.49 g, 17%); M.S. (M+H)⁺=304.

(b) N-[4-(((Diphenylamino)carbonyl)amino)phenyl]-2-thiophenecarboxamidine hydrochloride To a solution of the product of step (a) (0.49 g, 1.62 mmol) in isopropanol (10 ml) was added S-methyl-2-thiophenethiocarboximide hydroiodide (the product of Example 1, step (d)) (0.46 g, 1.62 mmol). The mixture was stirred for 48 hr, dumped into basic water and extracted with ethyl acetate (3×30 ml). The combined extracts were washed with water, dried over magnesium sulfate, filtered, and concentrated to an oil. Treatment with IPA/HCl yielded N-[4-(diphenylamino(carbonyl)amino]phenyl-2-thiophenecarboxamidine hydrochloride as a white solid: (24 m g, 3.3%); m.p. 210–211° C.

EXAMPLE 49

N-(3-((benzoyl)amino)phenyl)-2-thiophenecarboximidamide oxalate (a) N-(3-nitrophenyl)benzamide To a solution of 7.5 g (54 mmol) of 3-nitroaniline in a biphasic solution consisting of 100 ml of methylene chloride and 100 ml of 20% potassium carbonate was added dropwise 6.0 ml (52 mmol) of benzoyl chloride in 25 ml of methylene chloride. The reaction mixture was allowed to stir overnight and the organic phase was separated and washed with dilute hydrochloric acid. The solvent was concentrated to give 3.83 g (32%) of the title compound, MS 243 (M+H).

(b) N-(3-aminophenyl)benzamide

This compound was prepared following a process analogous to that of Example 30 step (b). MS 213 (M+H).

(c) N-(3-((benzoyl)amino)phenyl)-2-thiophenecarboximidamide oxalate

This compound was prepared following the procedure of Example 30, step (b). The free base was converted to the oxalate salt in isopropanol. MS 323 (M+H).

EXAMPLE 50

N-(4-((benzoyl)amino)phenyl)-2-thiophenecarboximidamide hydroiodide (a) N-(3-nitrophenyl)benzamide This compound was prepared following a process analogous to that of Example 49, step (a). MS 243 (M+H).

(b) N-(4-aminophenyl)benzamide

This compound was prepared following a process analogous to that of Example 30, step (b). MS 213 (M+H).

(c) N-(4-((benzoyl)amino)phenyl)-2-thiophenecarboximidamide hydroiodide

This compound was prepared following the procedure of Example 26, step (b) and was recrystallized from water, m.p. 234–5° C.

EXAMPLE 51

N-(3-(((phenylamino)carbonyl)amino)phenyl)-2-thiophenecarboximidamide oxalate (a) N-phenyl-N'-(3-nitrophenyl) urea To a solution of 5.0 g (36 mmol) of m-nitroaniline in 40 ml of ether was added 5.0 ml (47 mmol) of phenylisocyanate. The solution was stirred for 6 hours. The product was filtered to afford 9.2 g (99%) of the title compound. MS 258 (M+H).

(b) N-phenyl-N-'-(3-aminophenyl) urea

This compound was prepared by a process analogous to that of Example 30, step (b). Slurring the isolated product in ether afforded a solid product, m.p. 199–202° C.

(c) N-(3-(((phenylamino)carbonyl)amino)phenyl-2-thiophenecarboximidamide oxalate This compound was prepared following the procedure of Example 30, step (c). The free base was converted to the oxalate salt in isopropanol, 208–210° C.

EXAMPLE 52

N-(3-(((4-phenoxylbutyl)amino)carbonyl)phenyl)-2-thiophenecarboximidamide oxalate (a) 3-nitro-N-(4-phenoxybutyl)benzamide This compound was prepared following a process analogous to that of Example 49, step (a). MS 315 (M+H).

(b) N-((3-(4-phenoxybutyl)amino)carbonyl)aniline hydrochloride

A solution of 7.8 g (25 mmol) N-4-phenoxybutyl-3-nitrobenzamide and 1 g of 5% palladium on carbon in 120 ml of isopropanol with hydrogen chloride added was hydrogenated at 45 psi for 3 hr. The catalyst was filtered off and the solvent was concentrated to give 6.7 g (84%) of the title compound. MS 285 (M+H).

(c) N-(3-(((4-phenoxylbutyl)amino)carbonyl)phenyl)-2-thiophenecarboximidamide oxalate The above compound was first converted to the free base and the title compound was prepared using the procedure of Example 30, step (c). The free base of the title compound was then converted to the oxalate salt in isopropanol. MS 394 (M+H), m.p. 154–6° C.

EXAMPLE 53

N-(3-(((4-phenylbutyl)amino)carbonyl)phenyl)-2-thiophenecarboximidamide oxalate (a) 3-nitro-N-(4-phenylbutyl)benzamide This compound was prepared following a process analogous to that of Example 49, step (a). MS 299 (M+H).

(b) 3-amino-N-(4-phenylbutyl)benzamide hydrochloride

This compound was prepared following a process analogous to that of Example 52, step (b). MS 273 (M+H).

(c) N-(3-(((4-phenylbutyl)amino)carbonyl)phenyl)-2-thiophenecarboximidamide oxalate This compound was prepared following the procedure of Example 30, step (c) except an equivalent of triethylamine was also added. The free base was converted to the oxalate salt in isopropanol, MS 376 (M+H), m.p. 118–120° C.

EXAMPLE 54

N-(4-((((benzyl)amino)carbonyl)methyl)phenyl)-2-thiophenecarboximidamide (a) N-benzyl-(4-nitro)phenylacetamide This compound was prepared following a process analogous to that of Example 49, step (a), m.p. 172–82° C.

(b) N-benzyl-(4-amino)phenylacetamide

This compound was prepared following the procedure of Example 17, step (d), m.p. 137–140° C.

(c) N-(4-((((benzyl)amino)carbonyl)methyl)phenyl)-2-thiophenecarboximidamide

This compound was prepared following the procedure of Example 30, step (c), m.p. 157–161° C.

EXAMPLE 55

N-(4-(2-(1-pyrrolidinyl)ethyl)phenyl)-2-thiophenecarboximidamide dihydrobromide (a) N-pyrrolidinyl-(4-nitrophenyl)acetic acid To a solution of 3.12 g (43.9 mmol) of pyrrolidine in a biphasic solution consisting of 100 ml of methylene chloride and 100 ml of 20% potassium carbonate was added dropwise 7.3 g (36.5 mmol) of 4-nitrophenylacetyl chloride in 25 ml of methylene chloride. The reaction mixture was allowed to stir overnight and the organic phase was separated and washed with dilute hydrochloric acid. The solvent was concentrated to give 6.26 g (73%) of the title compound, m.p. 103–5° C.

(b) 4-(2-(1-pyrrolidinyl)ethyl)nitrobenzene

This compound was prepared following the procedure of Example 17, step (c). MS 221 (M+H).

(c) 4-(2-(1-pyrrolidinyl)ethyl)aniline

This compound was prepared following the procedure of Example 34, step (c). MS 191 (M+H).

(d) N-(4-(2-(1-pyrrolidinyl)ethyl)phenyl-2-thiophenecarboximidamide dihydrobromide This compound was prepared following the procedure of Example 18, step (b). The dihydrobromide salt was crystallised from isopropanol and ether, MS 300 (M+H).

EXAMPLE 56

N-(4-(2-(1-piperidinyl)ethyl)phenyl)-2-thiophenecarboximidamide dihydrochloride (a) N-piperidinyl-(4-nitrophenyl)acetic acid This compound was prepared following the procedure of Example 56, step (a), m.p. 105–7° C.

(b) N-(4-(2-(1-piperidinyl)ethyl)nitrobenzene

This compound was prepared following the procedure of Example 17, step (c), MS 235 (M+H).

(c) N-(4-(2-(1-piperidinyl)ethyl)aniline

This compound was prepared following the procedure of Example 34, step (c). The hydrochloride salt was converted to the free base as an oil, MS 205 (M+H).

(d) N-(4-(2-(1-piperidinyl)ethyl)phenyl)-2-thiophenecarboximidamide dihydrochloride This compound was prepared following the procedure of Example 34, step (d). The dihydrochloride salt was crystallised from isopropanol and ether, m.p. 256–61° C.

EXAMPLE 57

N-(4-(3-(1-pyrrolidinyl)propyl)phenyl)-2-thiophenecarboximidamide dioxalate (a) N-pyrrolidinyl-(4-nitrophenyl)propenamide This compound was prepared following the procedure of Example 55, step (a), MS 247 (M+H).

(b) 4-(2-(1-((pyrolidinyl)carbonyl)ethyl)aniline

This compound was prepared following the procedure of Example 34, step (c). MS 219 (M+H).

(c) 4-(3-(pyrolidinyl)propyl)aniline dihydrochloride

This compound was prepared following the procedure of Example 17, step (c). The dihydrochloride salt from ethanol, m.p. 262–5° C.

(d) N-(4-(3-(1-pyrrolidinyl)propyl)phenyl)-2-thiophenecarboximidamide dioxalate

This compound was prepared following the procedure of Example 18, step (b). The dioxalate salt was prepared from ethanol and ether, m.p. 86–92° C.

EXAMPLE 58

N-(4-(3-(1-piperidinyl)propyl)phenyl)-2-thiophenecarboximidamide, dioxalate (a) N-piperidinyl-(4-nitrophenyl)propenamide This compound was prepared following the procedure of Example 55, step (a), m.p. 168–71° C.

(b) 4-(2-(1-((piperidinyl)carbonyl)ethyl)aniline

This compound was prepared following the procedure of Example 34, step (c). MS 233 (M+H).

(c) N-(4-(2-(1-piperidinyl)propyl)aniline

This compound was prepared following the procedure of Example 17, step (c), m.p. 180–5° C.

(d) N-(4-(3-(1-piperidinyl)propyl)phenyl)-2-thiophenecarboximidamide dioxalate

This compound was prepared following the procedure of Example 17, step (e). The dioxalate salt was prepared from ethanol and ethyl acetate, MS 328 (M+H).

EXAMPLE 59

N-(4-(2-(2-(1,2,3,4-tetrahydro)isoquinolyl)ethyl)phenyl)-2-thiophenecarboximidamide dihydrobromide (a) 4-nitro-N-(2-isoquinolyl)phenylacetamide To a solution of 4-nitrophenylacetic acid (5.43 g 930 mmol) and 1,2,3,4-tetrahydroisoquinoline (5.6 g, 42 mmol) in methylene chloride (200 ml) was added 1-(3-dimethylaminopropyl)-3-ethyl carbodiimide hydrochloride (6.13 g, 32 mmol). The reaction mixture was allowed to stir for 18 hr. The reaction mixture was washed with dilute hydrochloric acid and dilute sodium hydroxide, dried, and the solvent was concentrated to give a solid. Trituration with ether give the title compound, m.p. 137–9° C.

(b) N-(4-(2-(2-(1,2,3,4-tetrahydro)isoquinolyl)ethyl)nitrobenzene

This compound was prepared following the procedure of Example 17, step (c), m.p. 97–102° C.

(c) N-(4-(2-(2-(1,2,3,4-tetrahydro)isoquinolyl)ethyl)aniline

This compound was prepared following the procedure of Example 34, step (c), m.p. 300° C. (dec).

(d) N-(4-(2-(2-(1,2,3,4-tetrahydro)isoquinolyl)ethyl)phenyl)-2-thiophenecarboximidamide dihydrobromide This compound was prepared following the procedure of Example 18, step (b). The dihydrobromide salt was prepared from ethanol and ethyl acetate. MS 362 (M+H).

EXAMPLE 60

N-(4-((((phenylmethyl)amino)methylcarbonyl)amino)phenyl)-2-thiophenecarboximidamide free base (a) N-(4-nitrophenyl)-2-chloroacetamide 4-nitroaniline (13.8 g) in ethyl acetate (200 ml) was treated with triethyl amine (15 ml) and then treated in portions with chloroacetyl chloride (8 ml). The resulting mixture was stirred for 10 minutes. The mixture was then treated with water (200 ml) and ethyl acetate (100 ml). The mixture was warmed until all solids were dissolved, and the layers separated. The ethyl acetate layer was then concentrated to 100 ml whilst hot, and cooled to room temperature. The next day the mixture was filtered, and the solids washed with ethyl acetate and air dried to give N-(4-nitrophenyl)-2-chloroacetamide, m.p. 183–185° C., 14.83 g.

(b) 4-((((phenylmethyl)amino)methylcarbonyl)amino)nitrobenzene

The compound of step (a) (4.28 g) and benzylamine (2.5 ml) were combined in DMF (10 ml) with potassium carbonate (3.2 g) and stirred at room temperature for 3 hours. The solids were filtered off, and washed with methanol (2×10 ml). The combined filtrates were slowly diluted with water to 150 ml to give yellow solids, which were collected by filtration, and air dried to give 4-((((phenylmethyl)amino)methylcarbonyl)amino)nitrobenzene, MS 286 (M+H).

(c) 4-((((phenylmethyl)(trifluoromethylcarbonyl)amino)methylcarbonyl)amino)nitrobenzene The compound of step (b) (4.9 g) trifluoroacetic anhydride (2.5 ml) and triethylamine (2.5 ml) were combined in ethyl acetate (50 ml), and the mixture with suspended solids was warmed to 50° C. overnight. The mixture was then washed with water (50 ml), filtered to remove solids, and the ethyl acetate layer was evaporated. The residue was taken up in ether (150 ml) and cooled to −20° C. overnight. The solids were collected by filtration to give 4-((((phenylmethyl)(trifluoromethylcarbonyl)amino)methylcarbonyl)-amino)-nitrobenzene, MS (M+H)=282.

(d) 4-((((phenylmethyl)(trifluoromethylcarbonyl)amino)methylcarbonyl)amino)aniline The compound of step (c) (3.8 g) was dissolved in ethyl acetate (50 ml) and ethanol (50 ml). The mixture was hydrogenated at 50 psi with palladium on carbon for 4 hours. The mixture was filtered and evaporated in vacuo to give white solids, 4-((((phenylmethyl)((trifluoromethylcarbonyl)amino)methylcarbonyl)amino)-aniline, MS (M+H)=352.

(e) N-(4-((((phenylmethyl)amino)methylcarbonyl)amino)phenyl)-2-thiophenecarboximidamide free base The compound of step (d) (1.05 g) and S-methyl-2-thiophenethiocarboximide hydroiodide (the product of Example 1 step (d)) (0.85 g) were treated with methanol (2 ml). After 15 minutes the solids had dissolved and the mixture was blown down with nitrogen to remove methanethiol. TLC with 10% isopropanol in chloroform on silica showed starting amine consumed and new spot of lower Rf. The mixture was dissolved in methanol (6 ml), and treated with potassium carbonate (1.1 g). The TLC with 15% methanol in chloroform on silica showed incomplete hydrolysis, so an additional 1.1 g of potassium carbonate was added. After 2 hours the conversion was complete, and the mix was filtered to remove solids. The next day the filtrate was treated with 0.65 g of maleic acid, diluted with ether and stirred overnight. The solids that were collected were not the desired product. The filtrate was further diluted with hexanes, and washed with water. The aqueous layer was treated with 1M potassium carbonate, and extracted with ethyl acetate. The ethyl acetate was evaporated in vacuo, and the residue taken up in 20 ml of methanol. The solution was treated slowly with water until solids precipitated. The solids were collected by filtration and dried at 40° C. under vacuum to give N-(4-((((phenylmethyl)amino)methylcarbonyl)amino)phenyl)-2-thiophenecarboximidamide, free base, m.p. 161–163° C.

EXAMPLE 61

N-(4-(2-(((2-Furanyl)methyl)amino)ethyl)phenyl)-2-thiophenecarboximidamide dioxalate (a) 4-Nitrophenyl acetyl chloride To 4-nitrophenyl acetic acid (30 g) was added thionyl chloride (100 ml). The mix was heated to reflux under nitrogen and stirred for two hours. The excess thionyl chloride was evaporated under vacuum, and the remaining oil was azeotropically dried with toluene. The resulting oil crystallized upon standing to leave 4-nitrophenyl acetyl chloride (35 g).

(b) 4-(2-(((2-Furanyl)methyl)amino)ethyl)nitrobenzene hydrochloride

To a stirred solution of furfurylamine (1.32 g) in methylene chloride (125 ml) at ° C. was added triethyl amine (2.36 ml), followed by the dropwise addition of a solution of the compound of step (a) (3.0 g) in methylene chloride (10 ml). The mixture was stirred at 0° C. for 15 minutes. The mixture was poured into water (150 ml) and the crude products extracted with methylene chloride (2×100 ml). The organic layers were collected, dried ($MgSO_4$), filtered and concentrated. The resulting solids were taken up in a solution of 7% methanol/methylene chloride, and purified on a silica gel column eluted with the same solvent. The product was collected and concentrated. The solid was taken up in THF (50 ml) and treated with 1M Borane/THF (50 ml). The solution was refluxed for 15 hours. The mixture was cooled to 0° C. and was slowly made acidic with 4N hydrochloric acid. The mixture was reheated to reflux and stirred for 4 hours. The excess acid and THF was evaporated under vacuum, and the remaining slurry was taken up in water (100 ml) and ethyl acetate (100 ml), made basic with 50% sodium hydroxide, and extracted with ethyl acetate (3×125 ml). The organic layers were collected dried ($MgSO_4$), filtered and concentrated. The crude product was purified on a silica gel column eluted with 10% methanol/methylene chloride. The product was collected and concentrated. The remaining solids were taken up in isopropyl alcohol (25 ml), and treated with saturated IPA/HCl (10 ml). The white solids were filtered and washed with isopropyl alcohol to give 4-(2-(((2-furanyl)methyl)amino)ethyl)nitrobenzene hydrochloride (2.9 g).

(c) 4-(2-(((2-furanyl)methyl)amino)ethyl) aniline dihydrochloride.

To a stirred solution of the compound of step (b) (2.46 g) in acetic acid (100 ml) was added of zinc dust (3.3 g) in one portion. The mixture was stirred for 10 minutes. The zinc was filtered and the excess acid evaporated under vacuum. The remaining solids were taken up in water (100 ml) and ethyl acetate (100 ml), made basic with 50% sodium hydroxide, and extracted with ethyl acetate (3×125 ml). The organic layers were collected, dried ($MgSO_4$), filtered and concentrated. The remaining oil was taken up in isopropyl alcohol (25 ml) and treated with saturated IPA/HCl (10 ml). The white solids were filtered and washed with isopropyl alcohol to leave 4-(2-(((2-furanyl) methyl)amino)ethyl) aniline dihydrochloride (1.50 g).

(d) N-(4-(2-((( 2-Furanyl)methyl)amino)ethyl)phenyl-2-thiophenecarboximidamide dioxalate To a stirred suspension of the compound of step (c) (1.5 g) in DMF (15 ml) was added pyridine (0.42 ml) followed by of S-methyl-2-thiophenecarboxamide hydroiodide (the product of Example 1 step (d)) (1.51 g). The mixture was heated to 50° C. and stirred for 48 hours. The mixture was then diluted in 100 ml water and made basic with excess 50% sodium hydroxide. The crude product was extracted with ethyl acetate (3×100 ml). The organic layers collected and washed with water (2×200 ml). The organic layer was dried ($MgSO_4$), filtered and concentrated. The crude product was purified on a silica gel column eluted with 20% methanol/methylene chloride. The product was collected and concentrated to an oil, which was taken up in isopropyl alcohol and treated with 2.5 equivalents of oxalic acid. The white solids were filtered and washed with ether to leave N-(4-(2-(((2-Furanyl)methyl)amino)ethyl)phenyl)-2-thiophenecarboximidamide dioxalate (580 mg) m.p. decomposes >220° C.

EXAMPLE 62

The following compounds were made following a process analogous to that of Example 61:

(a) N-(4-(2-(((2-Pyridyl)methyl)amino)ethyl)phenyl)-2-thiophenecarboximidamide trihydrochloride, m.p. decomposes >250° C.

(b) N-(4-(2-(((2-Thiophenyl)methyl)amino)ethyl)phenyl)-2-thiophenecarboximidamide dioxalate, m.p. decomposes >226° C.

EXAMPLE 63

N-(4-((amino)carbonyl)phenyl)-2-thiophenecarboximidamide hydroiodide

This compound was prepared following the procedure of Example 26, step (b). The salt was recrystallized from 30% isopropanol in water, m.p. 236° C. (dec).

EXAMPLE 64

N-(4-(((2-thienyl)carbonyl)amino)phenyl)-2-thiophenecarboximidamide oxalate (a) N-(4-nitrophenyl)-2-thiophenecarboxamide This compound was prepared using the procedure described in Example 26, step (a), MS 249 (M+H).

(b) N-(4-amino)aniline-2-thiophenecarboxamide

This compound was prepared using the procedure described for Example 17, step (d). MS 219 (M=H).

(c) N-(4-(((2-thienyl)carbonyl)amino)phenyl)-2-thiophenecarboximidamide oxalate

This compound was prepared following the procedure of Example 7, step (c). The free base was converted to the oxalate salt in isopropanol, m.p. 231–3° C.

EXAMPLE 65

N-[4-((((Diphenylamino)carbonyl)amino)methyl) phenyl)]-2-thiophenecarboxamidine oxalate (a) 4-((((Diphenylamino)carbonyl)amino)methyl) nitrobenzene To a stirred solution of 4-nitrobenzylamine hydrochloride (1.04 g, 5.51 mmol) and triethylamine (1.56 ml, 11.22 mmol) in methylene chloride (10 ml) was added diphenylcarbamyl chloride (1.40 g, 6.07 mmol). After stirring for 5 hr, the mixture was dumped into water and the layers separated. The aqueous layer was further extracted with methylene chloride (3×20 ml). The combined extracts were washed with water, dried ($MgSO_4$), filtered, and concentrated to yield a solid which was recrystallized from ethyl acetate/hexane/methanol to give 4-((((diphenylamino) carbonyl)amino)-methyl)nitrobenzene as a white solid: 1.37 g (72% yield); m.p. 137–138° C.

(b) 4-((((Diphenylamino)carbonyl)amino)methyl)aniline

To a stirred solution of the compound of step (a) (1.37 g, 3.94 mmol) in THF/MeOH (100 ml, 1:1) was added a catalytic amount of 10% Pd/C. The mixture was hydrogenated at 50 psi for 1 hr, filtered through celite, and concentrated to give 4-((((diphenylamino)carbonyl)amino)methyl) aniline which was homogeneous by TLC and used immediately in the next reaction.

(c) N-[4-((((Diphenylamino)carbonyl)amino)methyl) phenyl]-2-thiophenecarboxamidine oxalate To a solution of the compound of step (b) (1.24 g, 3.90 mmol) in isopropanol (10 ml) was added S-methyl-2-thiophenethiocarboximide hydroiodide (1.06 g, 3.70 mmol). The mixture was stirred for 18 hr, dumped into basic water and extracted with chloroform (3×30 ml). The combined extracts were washed with water, dried (MgSO$_4$), filtered, concentrated, and chromatographed over silica (6% methanol/methylene chloride) to an oil which solidified upon standing. A small amount was isolated as the oxalate salt: (48 mg); m.p. (dec) 150° C.

EXAMPLE 66

N-(4-((((2-thiophenyl)iminomethyl)amino)methyl) phenyl)-2-thiophenecarboxamidine difumarate a) 4-(aminomethyl)aniline To a solution of 4-nitrobenzylamine hydrochloride (9.0 g, 4.7 mmol) in methanol (200 ml) was added a catalytic amount of 10% palladium on carbon. The mixture was hydrogenated at 50 psi for 4 hours, filtered through celite, and concentrated to give a crude oil. The oil was dissolved in water (100 ml), and 20% sodium hydroxide (20 ml), was extracted twice with dichloromethane, the organic layer dried (MgSO$_4$), filtered and was concentrated to yield (6.1 g) of 4-(aminomethyl)aniline.

b) N-(4-((((2-thiophenyl)iminomethyl)amino)methyl) phenyl)-2-thiophenecarboxamidine difumarate A mixture of the compound of step (a) (1.6 g 1.3 mmol) and S-methyl-2-thiophenethiocarboximide hydroiodide (the product of Example 1, step (d)) (4.4 g, 1.5 mmol) in of DMF (10 ml) was warmed to 40° C. for 72 hours. The mixture was then diluted with 20% aqueous sodium hydroxide, and the solid collected by filtration of yield (2.5 g) of crude N-(4-((((2-thiophenyl)iminomethyl)amino)methyl)phenyl)-2-thiophenecarboxamidine. The difumarate salt was made from methanol and isopropanol. m.p. 200–201° C.

EXAMPLE 67

Following a process analogous to that of Example 66, the following compound was prepared:
(a) N-(4-((((2-thiophenyl)iminomethyl)amino)ethyl) phenyl)-2-thiophenecarboxamidine difumarate m.p. 200–201° C.

EXAMPLE 68

N-(4-((((3-methylphenyl)iminomethyl)amino)ethyl) phenyl)-2-thiophenecarboxamidine difumarate (a) N-(4-(2-aminoethyl)phenyl)-2-thiophenecarboxamidine To a solution of 4-aminoethyl aniline dihydrochloride (1.4 g, 6.6 mmol) and S-methyl-2-thiophenethiocarboximide hydroiodide (the product of Example 1, step (d)) (2.2 g, 7.9 mmol) in DMF (10 ml) was added pyridine (0.52 g, 6.6 mmol). The mixture was stirred at 40° C. for 24 hours, diluted with 20% aqueous sodium hydroxide, extracted twice with dichloromethane, dried (MgSO$_4$), filtered and concentrated to give N-(4-(2aminoethyl)phenyl)-2-thiophenecarboxamidine (4.1 g) as an oil.

(b) N-(4-((((3-methylphenyl)iminomethyl)amino)ethyl) phenyl)-2-thiophenecarboxamidine difumarate To a solution of the compound of step (a) (2.0 g, 8.2 mmol) was added S-methyl-(3-methylphenyl) thiocarboximide hydroiodide (2.8 g, 9.2 mmol) in isopropanol (10 ml). The mixture was stirred at 40° C. for 18 hours, diluted with 20% aqueous sodium hydroxide, and extracted twice with ethyl acetate. The organic layer was washed with water (100 ml), dried (MgSO$_4$) filtered and concentrated to give an oil. The difumarate salt was made from methanol, isopropanol, and ethyl acetate to yield N-(4-((((3-methylphenyl)iminomethyl)amino)ethyl) phenyl)-2-thiophenecarboxamidine difumarate: m.p.200–201° C.

EXAMPLE 69

Following a process analogous to that of Example 68, the following compound was prepared:
(a) N-(3-((((2-thiophenyl)iminomethyl)amino)ethyl) phenyl)-2-thiophenecarboxamidine difumarate. m.p. 211–212° C.

EXAMPLE 70

N-(4-(2-((pyrimidin-2-yl)amino)ethyl)phenyl)-2-thiophenecarboxamide dihydrochloride (a) [2-(4-nitrophenyl)ethyl]pyrimidi-2-ylamine To a solution of 4-nitrophenethylamine hydrochloride (2.0 g, 9.8 mmol) in dimethylformamide (20 ml) was added potassium carbonate (10 g) and 2-chloropyrimidine (1.6 g, 1.4 mmol). The mixture was heated to 100° C. for 24 hours, diluted with water (300 ml), extracted twice with ethyl acetate, dried (MgSO$_4$), filtered and concentrated to yield a crude solid. The monohydrochloride salt was made from ethyl acetate, isopropanol to yield (2.4 g) of [2-(4-nitrophenyl)ethyl]pyrimidi-2-ylamine hydrochloride.

(b) [2-(4-aminophenyl)-ethyl]pyrimidi-2-ylamine

To a solution of the compound of step (a) in acetic acid (100 ml) was added zinc dust (3.0 g). The reaction mixture was stirred for 30 minutes, filtered and concentrated. The residue was partitioned with 20% aqueous sodium hydroxide and dichloromethane and the organic layer was dried (MgSO$_4$), filtered and concentrated to yield 1.3 g of [2-(4-aminophenyl)-ethyl]pyrimidi-2-ylamine.

(c) N-(4-(2-((pyrimidin-2-yl)amino)ethyl)phenyl)-2-thiophenecarboxamide dihydrochloride To a solution of the compound of step (b) (1.3 g, 6.6 mmol) in (10 ml) of dimethylformamide was added S-methyl-2-thiophenethiocarboximide hydroiodide (the product of Example 1, step (d)). The reaction was stirred for 72 hours, diluted with 20% sodium hydroxide and extracted twice with ethyl acetate. The combined extracts were washed twice with water, dried (MgSO$_4$), filtered and concentrated. The hydrochloride salt was made from methanol and isopropanol to yield N-(4-(2-((pyrimidin-2-yl)amino) ethyl)phenyl)-2-thiophenecarboxamide dihydrochloride. m.p. 191–192° C.

EXAMPLE 71

N-(4-(2-((phenylmethyl)amino)ethoxy)-2-fluorophenyl)-2-thiophenecarboximidamide a) 3-fluoro-4-nitrophenoxyacetic acid A sample of 3-fluoro-4-nitrophenol (5.18 g) and potassium carbonate (10 g) was treated with DMF (20 ml). Ethyl bromoacetate (5 ml) was then added, and the mixture was stirred at 22° C. After two hours the mixture was treated with methanol (20 ml) and water (40 ml) and allowed to stir. After an additional two hours, the mixture was diluted with water to 200 ml and the solids filtered off. The filtrate was acidified and the solids collected to give 3-fluoro-4-nitrophenoxyacetic acid, m.p. 90–92° C.

b) N-phenylmethyl-3-fluoro-4-nitrophenoxyacetamide

A sample of the compound of step (a) (2.84 g) was dissolved in dry THF (100 ml), then methylmorpholine (1.45 ml) was added and the mix stirred at 0° C. Ethyl chloroformate, (1.26 ml) was added, and the mixture stirred for 2 minutes. Benzylamine (1.45 ml) was added, and the mixture as stirred at 0° C. After 15 minutes the mixture was diluted slowly with water to 220 ml and stirred at 0° C. The resulting solids were collected and washed with water then air dried to give N-phenylmethyl-3-fluoro-4-nitrophenoxyacetamide, m.p. 128.5–130° C.

(c) N-(4-(2-((phenylmethyl)amino)ethoxy)-2-fluorophenyl)-2-thiophenecarboximidamide The product of step (b) was converted to N-(4-(2-((phenylmethyl)amino) ethoxy)-2-fluoro-phenyl)-2-thiophenecarboximidamide free base following a process analogous to that of Example 19, steps (c) and (d); m.p. 105–107° C.

EXAMPLE 72

N-(4-(2-((phenylmethyl)(methyl)amino)ethyl)phenyl) trifluoroacetimidamide 4-(2-((phenylmethyl)(methyl)amino)ethyl)aniline dihydrochloride (prepared following method of Example 19, steps (a)–(c)) (1.03 g) was dissolved in water (25 ml), treated with 50% sodium hydroxide (5 ml), and extracted with ethyl ether. The extract was dried (NaOH), and evaporated to provide free base, 0.72 g. The free base was then treated with trifluoroacetimidamide, and warmed to 100° C. After one hour, toluene (5 ml) was added to improve stirring. The mixture was cooled after 2 hours, and water (30 ml) was added, and the mixture was stirred. After 15 minutes, the water was decanted from the resulting semisolid tan residue. The residue was recrystallised from a methanol and water mixture (125 ml), giving N-(4-(2-((phenylmethyl)(methyl)amino)ethyl)phenyl)-trifluoroacetimidamide, as a tan solid, m.p. 105–107° C.

What is claimed is:

1. A method of treatment or prophylaxis of diseases or conditions in which inhibition of NOS is beneficial which comprises administering to a person in need thereof a therapeutically effective amount of a compound of formula (I)

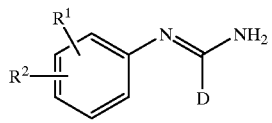

wherein
D represents phenyl, pyridinyl or a 5-membered heterocyclic aromatic ring containing 1 to 4 heteroatoms selected from O, S or N, which three groups are optionally substituted by one or more groups selected from alkyl C1 to 6, alkoxy C1 to 6, halogen and perfluoroalkyl C1 to 6; or perfluoroalkyl C1 to 6;

$R^1$ represents hydrogen, alkyl C1 to 6 or halogen $R^2$ represents $—X(CH_2)_nZCONR^3R^4$, $—X(CH_2)_nNHCO(CH_2)_sNR^3R^4$, $—X(CH_2)_pNR^3R^4$, $—X(CH_2)_nNHCOR^5$ or $—(CH_2)_qNHC(NH)R^6$;

$R^3$ and $R^4$ independently represent hydrogen, alkyl C1 to 6, $—(CH_2)_rA$, $—(CH_2)_mOA$ or $—CH(CH_3)(CH_2)_1A$; or $—NR^3R^4$ together represent 1-indanyl, piperonylamino-, piperdinyl, morpholinyl, pyrrolidinyl, 1,2,3,4-tetrahydroisoquinolinyl; or piperazinyl optionally 4-substituted by alkyl C1 to C6;

$R^5$ represents alkyl C1 to 6, perfluoroalkyl C1 to 6, $—(CH_2)_rA$ or $—O(CH_2)_wA$;

A represents phenyl, pyridinyl, pyrimidinyl, or a 5 membered heterocyclic aromatic ring containing 1 to 4 heteroatoms selected from O, S and N, which four groups are optionally substituted by one or more groups selected from alkyl C1 to 6, halogen, nitro, cyano and trifluoromethyl;

$R^6$ represents phenyl, pyridinyl or a 5 membered heterocyclic aromatic ring containing 1 to 4 heteroatoms selected from O, S and N, which three groups are optionally substituted by one or more groups selected from alkyl C1 to 6, alkoxy C1 to 6, halogen and perfluoroalkyl C1 to 6; or perfluoroalkyl C1 to 6;

n and r independently represent an integer in the range 0 to 6 inclusive;

p and w independently represent an integer in the range 1 to 5 inclusive;

m represents an integer in the range 2 to 5 inclusive;

q and t independently represent an integer in the range 0 to 5 inclusive;

s represents an integer in the range 1 to 3 inclusive;

X represents O or a bond;

Z represents O, $NR^7$ or a bond;

$R^7$ represents hydrogen or alkyl C1 to 6;

provided that:
(a) when D contains a heteratom, it is not connected to the remainder of the compound of formula I through the heteroatom;
(b) when $R^2$ represents $—X(CH_2)_nZCONR^3R^4$, and neither X nor Z represent a bond, then n represents an integer in the range 2 to 6 inclusive;
(c) when $R^2$ represent $—X(CH_2)_nNHCO(CH_2)_sNR^3R^4$, or $—X(CH_2)_nNHCOR^5$, and X represents O, then n represents an integer in the range 2 to 6 inclusive;
(d) when $R^2$ represents $—X(CH_2)_pN^3R^4$ and X represents O, then p represents an integer in the range 2 to 5 inclusive; or a pharmaceutically acceptable salt thereof.

2. A method according to claim 1 in which $R^2$ represents $—X(CH_2)_pNR^3R^4$ or $—(CH_2)_qNHC(NH)R^6$, and X represents a bond.

3. A method according to claim 1 in which the compound of formula (I) is N-(3-(((phenylmethyl)amino)methyl)phenyl)-2-thiophenecarboximidamide or a pharmaceutically acceptable salt thereof.

4. A method according to claim 1 in which the compound of formula (I) is N-(3-(2-(2-(1,2,3,4-tetrahydro)isoquinolinyl)ethyl)phenyl)-2-thiophenecarboximidamide or pharmaceutically acceptable salt thereof.

5. A method according to claim 1 in which the compound of formula (I) is N-(4-(2-(((3-chlorophenyl)methyl)amino)ethyl)phenyl)-2-thiophenecarboxamidine or a pharmaceutically acceptable salt thereof.

6. A method according to claim 1 in which the compound of formula (I) is N-(4-(((4-chlorophenyl)iminocarbonyl)amino)phenyl)-2-pyrrolecarboximidamide or a pharmaceutically acceptable salt thereof.

7. A method according to claim 1 in which the compound of formula (I) is N-(4-(2-(1-piperidinyl)ethyl)phenyl)-2-thiophenecarboximidamide or a pharmaceutically acceptable salt thereof.

8. A method according to claim 1 in which it is predominantly the neuronal isoform of NOS that is inhibited.

9. A method according to claim 1 in which the compound of formula (I) is administered in the form of a pharmaceutical composition.

10. A method according to claim 1 in which the disease or condition is stroke.

11. A method according to claim 1 in which the disease or condition is schizophrenia.

12. A method according to claim 1 in which the disease or condition is anxiety.

13. A method according to claim 1 in which the disease or condition is pain.

14. A pharmaceutical composition comprising N-(3-(((phenylmethyl)amino)methyl)phenyl)-2-thiophenecarboximidamide or a pharmaceutically acceptable salt thereof in a pharmaceutically acceptable diluent or carrier for oral or parenteral administration.

15. A pharmaceutical composition comprising N-(3-(2-(2-(1,2,3,4-tetrahydro)isoqinolinyl)ethyl)phenyl)-2-thiophenecarboximidamide or a pharmaceutically acceptable salt thereof in a pharmaceutically acceptable diluent or carrier for oral or parenteral administration.

16. A pharmaceutical composition comprising N-(4-(2-(((3-chlorophenyl)methyl)amino)ethyl)phenyl)-2-thiophenecarboximidamide or a pharmaceutically acceptable salt thereof in a pharmaceutically acceptable diluent or carrier for oral or parenteral administration.

17. A pharmaceutical composition comprising N-(4-(((4-chlorophenyl)iminocarbonyl)amino)phenyl)-2-pyrrolecarboximidamide or a pharmaceutically acceptable salt thereof in a pharmaceutically acceptable diluent or carrier for oral or parenteral administration.

18. A pharmaceutical composition comprising N-(4-(2-(1-piperidinyl)ethyl)phenyl)-2-thiophenecarboximidamide or a pharmaceutically acceptable salt thereof in a pharmaceutically acceptable diluent or carrier for oral or parenteral administration.

* * * * *